(12) United States Patent
Garcia Castro et al.

(10) Patent No.: US 8,173,583 B2
(45) Date of Patent: May 8, 2012

(54) USE OF CATIONIC COPOLYMERS OF AMINE-CONTAINING ACRYLATES AND N-VINYLIMIDAZOLIUM SALTS IN HAIR COSMETIC PREPARATIONS

(75) Inventors: Ivette Garcia Castro, Ludwigshafen (DE); Gabi Winter, Shanghai (CN); Claudia Wood, Weinheim (DE)

(73) Assignee: BASF SE, Ludwigshafen (DE)

( * ) Notice: Subject to any disclaimer, the term of this patent is extended or adjusted under 35 U.S.C. 154(b) by 132 days.

(21) Appl. No.: 12/377,203

(22) PCT Filed: Aug. 6, 2007

(86) PCT No.: PCT/EP2007/058121
§ 371 (c)(1),
(2), (4) Date: Feb. 11, 2009

(87) PCT Pub. No.: WO2008/017653
PCT Pub. Date: Feb. 14, 2008

(65) Prior Publication Data
US 2010/0179082 A1 Jul. 15, 2010

(30) Foreign Application Priority Data
Aug. 11, 2006 (EP) .................................. 06118775

(51) Int. Cl.
*C11D 3/37* (2006.01)
*A61Q 5/00* (2006.01)
*A61K 8/72* (2006.01)

(52) U.S. Cl. ........ 510/119; 510/123; 510/475; 510/500; 510/504; 424/401; 424/70.122

(58) Field of Classification Search .................. 510/119, 510/123, 475, 500, 504; 424/401, 70.122
See application file for complete search history.

(56) References Cited

U.S. PATENT DOCUMENTS

| | | | |
|---|---|---|---|
| 3,405,084 A | 10/1968 | Bohac et al. | |
| 4,841,066 A | 6/1989 | Goertz et al. | |
| 5,580,494 A | 12/1996 | Sandhu et al. | |
| 5,935,561 A | 8/1999 | Inman et al. | |
| 6,355,231 B1 * | 3/2002 | Dieing et al. ............ | 424/70.1 |
| 6,998,113 B1 | 2/2006 | Traynor et al. | |

FOREIGN PATENT DOCUMENTS

| | | |
|---|---|---|
| DE | 1165574 | 3/1964 |
| DE | 2024051 | 12/1971 |
| DE | 2150557 | 6/1972 |
| DE | 2817369 | 10/1978 |
| DE | 3708451 | 10/1988 |
| DE | 3929973 | 3/1991 |
| DE | 4223066 | 1/1994 |
| DE | 4225045 A1 | 2/1994 |
| DE | 4333238 | 4/1995 |
| DE | 19745637 | 4/1999 |
| DE | 19838851 | 3/2000 |
| DE | 10318526 | 11/2004 |
| EP | 246 580 | 11/1987 |
| EP | 0257444 | 3/1988 |
| EP | 0480280 | 4/1992 |
| EP | 0636361 | 2/1995 |
| EP | 0751162 | 1/1997 |
| EP | 911 018 | 4/1999 |
| EP | 0934956 | 8/1999 |
| JP | 57-210083 | 12/1982 |
| WO | WO-94 06403 | 3/1994 |
| WO | WO-94 06409 | 3/1994 |
| WO | WO-9725021 | 7/1997 |
| WO | WO-00 68282 | 11/2000 |
| WO | WO-03092640 | 11/2003 |

OTHER PUBLICATIONS

Database WPI Week 198306 Derwent Publications Ltd., London, GB; AN 1983-13366K XP002458838 & JP 57 210083 A (Nikka Kagau Kogyo) Dec. 23, 1982.

* cited by examiner

*Primary Examiner* — Brian P Mruk
(74) *Attorney, Agent, or Firm* — Connolly Bove Lodge & Hutz LLP

(57) ABSTRACT

The present invention relates to the use of cationic polymers obtainable by free-radical copolymerization of a) 60 to 99 mol % of at least one 1-vinylimidazole monomer, b) 1 to 40 mol % of at least one free-radically polymerizable quaternizable monomer b1) or methacrylic acid b2) and c) 0 to 30 mol % of at least one further free-radically copolymerizable monomer different from a) and b) in hair cosmetic preparations.

14 Claims, No Drawings

USE OF CATIONIC COPOLYMERS OF AMINE-CONTAINING ACRYLATES AND N-VINYLIMIDAZOLIUM SALTS IN HAIR COSMETIC PREPARATIONS

CROSS REFERENCE TO RELATED APPLICATIONS

This application is a national phase of PCT/EP2007/058121, filed on Aug. 6, 2007, which claims priority to EP0611.8775.3, filed on Aug. 11, 2006, the entire contents of which are incorporated herein by reference.

The present invention relates to the use of cationic polymers obtainable by free-radical copolymerization of a) 60 to 99 mol % of at least 1-vinylimidazole monomer, b) 1 to 40 mol % of at least one free-radically polymerizable quaternizable monomer b1) or methacrylic acid b2) and c) 0 to 30 mol % of at least one further free-radically copolymerizable monomer different from a) and b) in hair cosmetic preparations, in particular as conditioners in shampoos.

Furthermore, the present invention relates to shampoos and other haircare compositions comprising the cationic polymer. Accordingly, the invention relates to compositions for the cleansing and/or care of the hair.

In particular, apart from shampoos, the invention also relates to further haircare compositions which are selected from the group consisting of pretreatment compositions, hair rinses, hair conditioners, hair balms, leave-on hair treatments, rinse-off hair treatments, hair tonics, pomades, styling creams, styling lotions, styling gels, end fluids, hot-oil treatments and foam treatments.

PRIOR ART

Haircare compositions serve primarily to improve the dry and wet combability, the feel to the touch, the shine and the appearance of the hair, and also to impart antistatic properties to the hair.

A shampoo should lather and cleanse the hair well, be mild and compatible and also practicable and pleasant to handle, it must also contribute to the care of the hair or to the elimination of hair and scalp problems. These additional effects and the cleansing effect, which has become self-evident, are characteristic of a modern shampoo. Cleansing power and foamability, skin compatibility, ability to be thickened and hydrolysis stability of the individual ingredients of shampoos are heavily dependent on the pH. The ingredients used in shampoos should optimally develop these properties in the neutral and weakly acidic pH range (pH 5-7), but outside of this pH range should also exhibit no significant losses in performance. The selected ingredients of the shampoos must be chemically stable and compatible with all of the other formulation constituents so that, for example, no reductions in effect or separations take place. Shampoos are expected to have an adequate cleansing power coupled with not too strong a degreasing effect and simultaneously adequate mildness. It is important that the cleansing power and the other desired surfactant properties are present both in soft water and in hard water. Shampoos have to be well tolerated by skin and mucosa and must therefore have no aggressive effect under the customary use conditions. A good cleansing performance does not have to be linked to considerable foam formation. Nevertheless, foam quantity and quality of the shampoos during washing represent important criteria for the consumer which have to be satisfied by the shampoos.

Besides the cleansing effect, shampoos also have a conditioning function which is ensured through the content of conditioners in the shampoo. Conditioners are auxiliaries which attach to the hair and remain on the hair even after the rinsing process. They lead to an improvement in combability, feel and shine of the hair. In the case of certain hair types (fine hair) or overdosing, however, the conditioners can also lead to undesired weighing down of the hair. From a formulation point of view, this means that when using conditioners, it is always necessary to ensure a good balance between conditioning performance and weighing-down of the hair. Furthermore, when using conditioners, it should also be ensured that the regular application of the product does not lead to a continuously growing amount of conditioners on the hair (build-up effect). The provision of products with a complex profile of properties often presents difficulties. Such complex property profiles often require the use of many different ingredients in one preparation, which in turn implies the risk of incompatibility toward one or more of these ingredients on the part of the consumer.

Conditioners in shampoos are primarily silicones and cationic polymers.

Silicones have the disadvantage that they are mostly water-insoluble and the shampoo formulation has to be stabilized through dispersants. These additives are often undesired. In addition, silicones sometimes exhibit considerable build-up effects and, following repeated use, the hair feels unpleasantly weighed down.

Many cationic polymers which are used as conditioners in shampoos, such as, for example, cationic cellulose derivatives, form surfactant-polymer complexes with anionic surfactants in the shampoo formulation; these are water-insoluble if the charge density of the polymers is high. For this reason, use is usually made of cationic polymers with low charge density so that they are soluble in the formulation.

However, cationic polymers with a high charge density have a greater affinity to the hair, for which reason it is desirable to use highly charged polymers in shampoos. However, the surfactant-polymer complexes in the formulation are then insoluble. The formulation has to be stabilized through the addition of dispersion auxiliaries.

WO 94/06403 describes the use of, inter alia, copolymers of N-vinylpyrrolidone and 3-methyl-1-vinylimidazolium salts with high charge density in combination with further water-insoluble conditioners in shampoo formulations. Accordingly, dispersants are used for stabilizing the formulations.

WO 94/06409 and U.S. Pat. No. 5,580,494 describe shampoo compositions based on an alpha-olefinsulfonate as detergent and a cationic polymer with a high charge density, e.g. copolymers of N-vinylpyrrolidone and 3-methyl-1-vinylimidazolium salts as conditioners. Dispersion auxiliaries also have to be added here to stabilize the formulations.

EP-A 246 580 describes that quaternized vinylimidazole copolymers with various other monomers are used as hair conditioners. The polymers described therein have the disadvantage that, in the case of a low fraction of the quaternized vinylimidazole monomers in the presence of anionic surfactants, they a low effect, and in the case of a high fraction of the quaternized vinylimidazole, no stable dispersions form.

EP-A 911 018 describes the use of cationic copolymers obtainable by free-radically initiated copolymerization of (a) 60 to 99 mol %, preferably 65 to 95 mol % and, particularly preferably, 70 to 90 mol % of an optionally substituted 1-vinylimidazole or a quaternized 1-vinylimidazole, (b) 1 to 40 mol %, preferably 5 to 35 mol %, particularly preferably 10 to 30 mol %, of an acid comprising a polymerizable double bond, or salts thereof and (c) 0 to 30 mol %, preferably 0 to 20 mol %, particularly preferably 0 to 10 mol % of a further free-radically copolymerizable monomer and subsequent quaternization of the polymer if a nonquaternized 1-vinylimidazole is used as monomer (a), as active ingredients in hair cosmetic preparations, in particular as conditioners in shampoos.

There is therefore a need for shampoos and haircare compositions which are well tolerated and which at the same time impart to the hair good sensorily detectable properties, such as elasticity, a pleasant feel and volume, without a good conditioning and cleansing effect being accompanied by an unsatisfactory greasy and/or sticky appearance of the hair treated therewith.

The aim was to develop shampoos and haircare compositions with the above-mentioned properties on the basis of the fewest possible feed materials since, in the case of compositions from the prior art, the large number of necessary components sometimes leads to skin irritations, allergic reactions and other incompatibilities. Particularly in the field of children and baby shampoos and haircare compositions, there is also a requirement for compositions with the smallest possible number of different ingredients.

It was an object of the present invention to find cationic polymers with high charge density which make it possible to prepare, without additional dispersion auxiliaries, stable shampoo formulations containing anionic surfactants.

This object was achieved through use of cationic polymers obtainable by free-radical copolymerization of a) 60 to 99 mol % of at least one 1-vinylimidazole monomer of the general formula I which is quaternized to at least 60 mol %

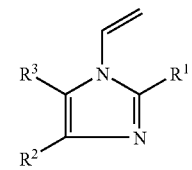
(I)

where $R^1$ to $R^3$, independently of one another, are hydrogen, $C_1$-$C_4$-alkyl or phenyl;

b) 1 to 40 mol % of at least one free-radically polymerizable monomer selected from b1) if appropriate quaternized compounds of the general formula II

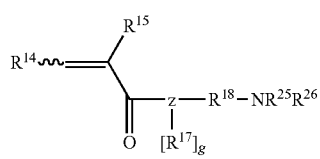
(II)

where
$R^{14}$ and $R^{15}$, independently of one another, are selected from the group consisting of hydrogen, $C_1$-$C_8$ linear- or branched-chain alkyl, methoxy, ethoxy, 2-hydroxyethoxy, 2-methoxyethoxy and 2-ethoxyethyl,
$R^{17}$ is hydrogen or methyl,
$R^{18}$ is alkylene or hydroxyalkylene having 1 to 24 carbon atoms, optionally substituted by alkyl, preferably $C_2H_4$, $C_3H_6$, $C_4H_8$, $CH_2$—$CH(OH)$—$CH_2$,
g is 0 or 1,
Z is nitrogen when g=1 or oxygen when g=0,
$R^{25}$ and $R^{26}$, in each case and independently of one another, are selected from the group consisting of hydrogen, $C_1$-$C_{40}$ linear- or branched-chain alkyl, formyl, $C_1$-$C_{10}$ linear- or branched-chain acyl, N,N-dimethylaminoethyl, 2-hydroxyethyl, 2-methoxyethyl, 2-ethoxyethyl, hydroxypropyl, methoxypropyl, ethoxypropyl or benzyl
b2) methacrylic acid
b3) mixtures of b1) and b2)
c) 0 to 30 mol % of at least one further free-radically copolymerizable monomer different from a) and b),
with the proviso that the amount c) is greater than 0 mol % when b) is methacrylic acid b2), where the total amount of the monomers a) to c) is 100 mol %, in hair cosmetic preparations.

a) 1-Vinylimidazole Monomers

Preference is given to N-vinylimidazoles of the general formula (I) in which $R^1$ to $R^3$ are hydrogen, $C_1$-$C_4$-alkyl or phenyl

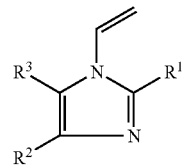
(I)

Examples of compounds of the general formula (I) can be found in the table below:

| $R^1$ | $R^2$ | $R^3$ |
|---|---|---|
| H | H | H |
| Me | H | H |
| H | Me | H |
| H | H | Me |
| Me | Me | H |
| H | Me | Me |
| Me | H | Me |
| Ph | H | H |
| H | Ph | H |
| H | H | Ph |
| Ph | Me | H |
| Ph | H | Me |
| Me | Ph | H |
| H | Ph | Me |
| H | Me | Ph |
| Me | H | Ph |

Me = methyl
Ph = phenyl

Particular preference as monomer a) is given to N-vinylimidazole, i.e. the compound of the formula I, where all of the radicals $R^1$ to $R^3$ are hydrogen.

Monomer a) is copolymerized in an amount of at most 99 mol %, preferably at most 90 mol %, particularly preferably at most 85 mol % and at least 60 mol %, preferably at least 65 mol %, particularly preferably at least 70 mol %, calculated as nonquaternized monomer, based on the total amount of the monomers a) to c).

The 1-vinylimidazole monomers a) are used for the polymerization in a form quaternized to at least 60 mol %. If appropriate, the resulting polymers are further quaternized when the polymerization has finished. In this connection, the polymerization is deemed to have finished when at least 90% by weight, preferably at least 95% by weight and in particular at least 99% by weight, of the monomers a) to c) used have polymerized.

The degree of quaternization (mol % of quaternized groups of all quaternizable groups) is at least 60%, preferably at least 70%, particularly preferably at least 80% and in particular at least 90%. Very particular preference is given to all quaternizable groups being quaternized, i.e. to a degree of quaternization of 100 mol %, based on the quaternizable groups. The quaternizing agent can of course also be added in excess. Of suitability for quaternizing the monomers a) or the resulting polymers are, for example, alkyl halides having 1 to 24 carbon atoms in the alkyl group, e.g. methyl chloride, methyl bromide, methyl iodide, ethyl chloride, ethyl bromide, propyl chloride, hexyl chloride, dodecyl chloride, lauryl chloride, propyl bromide, hexyl bromide, dodecyl bromide, lauryl bromide and benzyl halides, in particular benzyl chloride and benzyl bromide. For the quaternization with long-chain alkyl radicals, the corresponding alkyl bromides, such as hexyl bromide, dodecyl bromide or lauryl bromide, are preferred. Further suitable quaternizing agents are dialkyl sulfates, in particular dimethyl sulfate or diethyl sulfate.

The quaternization of the monomers a) can also be carried out with alkylene oxides, such as ethylene oxide or propylene oxide, in the presence of acids.

Preferred quaternizing agents are methyl chloride, dimethyl sulfate or diethyl sulfate, with methyl chloride and dimethyl sulfate being particularly preferred.

The quaternization of the monomers or polymers with one of the specified quaternizing agents takes place in accordance with customary methods known to the person skilled in the art.

b) Monomers b)

Preferred monomers b1) are esters of (meth)acrylic acid with amino alcohols that are mono- or di-$C_1$-$C_{24}$-alkyl-substituted on the nitrogen. Particular preference is given to those selected from the group consisting of N-methylaminoethyl (meth)acrylate, N-ethylaminoethyl (meth)acrylate, N-(n-propyl)aminoethyl (meth)acrylate, N-(n-butyl)aminoethyl (meth)acrylate, N-(tert-butyl)aminoethyl (meth)acrylate, N,N-dimethylaminomethyl (meth)acrylate, N,N-dimethylaminoethyl (meth)acrylate, N,N-diethylaminoethyl (meth)acrylate, N,N-dimethylaminopropyl (meth)acrylate, N,N-diethylaminopropyl (meth)acrylate and N,N-dimethylaminocyclohexyl (meth)acrylate. Particular preference is given to N,N-dimethylaminoethyl methacrylate.

The amides may be present in unsubstituted form, in N-alkyl or N-alkylamino-mono substituted form or in N,N-dialkyl-substituted or N,N-dialkylamino-disubstituted form, in which the alkyl or alkylamino groups are derived from $C_1$-$C_{40}$ linear, $C_3$-$C_{40}$ branched-chain, or $C_3$-$C_{40}$ carbocyclic units.

Further preferred monomers b1) are amides of (meth)acrylic acid with diamines that are mono- or di-$C_1$-$C_{24}$-alkyl-substituted on the nitrogen. Particular preference is given to those selected from the group consisting of N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide, N-[8-(dimethylamino)octyl]methacrylamide, N-[12-(dimethylamino)dodecyl]methacrylamide, N-[3-(diethylamino)propyl]methacrylamide and N-[3-(diethylamino)propyl]acrylamide. Particular preference is given to N-[3-(dimethylamino)propyl]methacrylamide.

As monomer b), it is also possible to use b2) methacrylic acid, where in this case the amount of monomer c) is obligatorily greater than 0 mol % and preferably at least one monomer c) is a monoethylenically unsaturated free-radically polymerizable compound.

A mixture of b1) and b2) can also be used as monomer b).

Monomer b) is copolymerized in an amount of at most 40 mol %, preferably at most 35 mol %, particularly preferably at most 30 mol % and at least 1 mol %, preferably at least 5 mol %, particularly preferably at least 10 mol % and in particular at least 12 mol %, based on the total amount of the monomers a) to c).

Monomer b1) can be used for the polymerization in quaternized form, although it is preferred to use monomer b1) in essentially nonquaternized form. Essentially nonquaternized means that at most 20 mol %, preferably at most 10 mol %, particularly preferably at most 5 mol % and in particular at most 1 mol %, of monomer b1) are present in quaternized form. It is most preferred if monomer b1) is not quaternized.

Monomer c)

Suitable monomers (c) are all free-radically copolymerizable monomers different from a) and b) which can be copolymerized with the monomers (a) and (b). For example, N-vinyllactams, e.g. N-vinylpiperidone, N-vinylpyrrolidone or N-vinylcaprolactam, and also N-vinylacetamide, N-methyl-N-vinylacetamide, acrylamide, methacrylamide, N,N-dimethylacrylamide, N-methylolmethacrylamide, N-vinylformamide, N-vinyl-oxazolidone, N-vinyltriazole, hydroxyalkyl (meth)acrylates, e.g. hydroxyethyl (meth)acrylate and hydroxypropyl (meth)acrylate, or alkyl ethylene glycol (meth)acrylates with 1 to 50 ethylene glycol units in the molecule are suitable. Mention is also to be made of $C_1$- to $C_{24}$-, in particular $C_1$- to $C_{10}$-alkyl esters of acrylic acid or methacrylic acid, e.g. methyl acrylate, methyl methacrylate, ethyl acrylate, ethyl methacrylate, tert-butyl acrylate, tert-butyl methacrylate, isobutyl acrylate, n-butyl acrylate and acrylamides, such as N-tert-butylacrylamide or N-tert-octylacrylamide. Furthermore, carboxylic acid vinyl esters, e.g. vinyl acetate or vinylpropionate, can be used.

Monomer c) is preferably selected from compounds of the general formula III

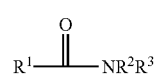

(III)

where
$R^1$ is a group of the formula $CH_2=CR^4$— where $R^4$=H or $C_1$-$C_4$-alkyl, and $R^2$ and $R^3$, independently of one another, are H, alkyl, cycloalkyl, heterocycloalkyl, aryl or hetaryl, or $R^2$ and $R^3$, together with the nitrogen atom to which they are bonded, are a five- to eight-membered nitrogen heterocycle or
$R^2$ is a group of the formula $CH_2=CR^4$— and $R^1$ and $R^3$, independently of one another, are H, alkyl, cycloalkyl, heterocycloalkyl, aryl or hetaryl, or $R^1$ and $R^3$, together with the amide group to which they are bonded, are a lactam having 5 to 8 ring atoms.

Preferably, the polymer used according to the invention additionally comprises, as monomer c), at least one N-vinyllactam in copolymerized form. Suitable as N-vinyllactam c) are unsubstituted N-vinyllactams and N-vinyllactam derivatives, which can, for example, have one or more $C_1$-$C_6$-alkyl substituents, such as methyl, ethyl, n-propyl, isopropyl, n-butyl, sec-butyl, tert-butyl, etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam, and mixtures thereof.

Preferably, the polymer suitable for the use according to the invention comprises monomers c) in incorporated form, where, in formula III, $R^2$ is $CH_2=CH-$ and $R^1$ and $R^3$, together with the amide group to which they are bonded, are a lactam having 5 ring atoms.

Particular preference is given to using N-vinylpyrrolidone, N-vinylcaprolactam, N-vinylformamide, (meth)acrylamide or mixtures thereof, where N-vinylpyrrolidone and methacrylamide are most preferred.

As monomers a), b) and c), it is of course also possible to use mixtures of the respective monomers, i.e., for example, as monomer c), a mixture of N-vinylpyrrolidone and N-vinylcaprolactam.

Monomer c) is not automatically used for preparing the polymers suitable for the use according to the invention unless monomer b) is methacrylic acid.

If monomer c) is copolymerized, then it is in an amount of at most 30 mol %, preferably at most 20 mol %, particularly preferably at most 15 mol %, in particular at most 10 mol % and preferably at least 0.1 mol %, particularly preferably at least 1 mol %, in particular at least 3 mol % and most preferably 5 mol %, based on the total amount of the monomers a) to c).

Polymerization

Polymerization

To prepare the polymers, the mixture of components a) to c) to be polymerized can be polymerized both with the help of initiators that form free radicals, and through the action of high-energy radiation, under which should also be understood the action of high-energy electrons.

Initiators for the free-radical polymerization which can be used are the peroxo and/or azo compounds customary for this purpose, for example alkali metal or ammonium peroxydisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxydicarbamate, bis(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidonopropane) dihydrochloride or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate.

Preferably, organic peroxides are used.

The polymerization can also be carried out through the action of ultraviolet radiation, if appropriate in the presence of UV initiators. For polymerization under the action of UV rays, the photoinitiators or sensitizers customarily suitable for this purpose are used. These are, for example, compounds such as benzoin and benzoin ether, α-methylbenzoin or α-phenylbenzoin. So-called triplet sensitizers, such as benzyl diketals, can also be used. Serving as UV radiation sources are, for example, besides high-energy UV lamps, such as carbon arc lamps, mercury vapor lamps or xenon lamps, also low-UV light sources, such as fluorescent tubes with a high blue fraction.

The amounts of initiator or initiator mixtures used, based on monomer used, are between 0.01 and 10% by weight, preferably between 0.1 and 8% by weight.

The polymerization takes place in the temperature range from 30 to 200° C., preferably in the range from 40 to 140° C., particularly preferably in the range from 50 to 110° C. It is usually carried out under atmospheric pressure, but can also proceed under reduced or increased pressure, preferably between 1 and 5 bar.

The polymerization can be carried out, for example, as solution polymerization, bulk polymerization, emulsion polymerization, inverse emulsion polymerization, suspension polymerization, inverse suspension polymerization or precipitation polymerization, without the methods which can be used being limited thereto.

The polymerization can also be carried out semicontinuously by firstly introducing some, e.g. about 10%, of the mixture to be polymerized and initiator, heating the mixture to polymerization temperature and, after the polymerization has started, adding the remainder of the mixture to be polymerized according to the progress of the polymerization.

The polymerization described above is preferably also carried out in a solvent. Suitable solvents are, for example, water, alcohols, such as methanol, ethanol, n-propanol, isopropanol, n-butanol, sec-butanol, tert-butanol, n-hexanol and cyclohexanol, and also glycols, such as ethylene glycol, propylene glycol and butylene glycol, and the methyl or ethyl ethers of the dihydric alcohols, diethylene glycol, triethylene glycol, glycerol, dioxane, butyl acetate, ethyl acetate and toluene, where water, alcohols and mixtures thereof are particularly preferred. In particular, the solvent used is water or an aqueous-ethanolic mixture.

Regulators

The free-radical polymerization of the monomer mixture can take place in the presence of at least one molecular weight regulator. Regulators are used preferably in a use amount of from 0.0005 to 5% by weight, particularly preferably from 0.001 to 2.5% by weight and in particular from 0.01 to 1.5% by weight, based on the total weight of monomers a) to c).

Regulators is the term generally used to refer to compounds with high transfer constants. Regulators increase the rate of chain transfer reactions and thus bring about a reduction in the degree of polymerization of the resulting polymers without influencing the gross reaction rate.

In the case of the regulators, a distinction can be made between mono-, bi- or polyfunctional regulators, according to the number of functional groups in the molecule which can lead to one or more chain transfer reactions. Suitable regulators are described in detail, for example, by K. C. Berger and G. Brandrup in J. Brandrup, E. H. Immergut, Polymer Handbook, 3rd Edition, John Wiley & Sons, New York, 1989, pp. II/81-II/141.

Suitable regulators are, for example, aldehydes such as formaldehyde, acetaldehyde, propionaldehyde, n-butyraldehyde or isobutyraldehyde.

Furthermore, regulators which can also be used are: formic acid, its salts or esters, such as ammonium formate, 2,5-diphenyl-1-hexene, hydroxylammonium sulfate, and hydroxylammonium phosphate.

Further suitable regulators are halogen compounds, e.g. alkyl halides, such as tetrachloromethane, chloroform, bromotrichloromethane, bromoform, allyl bromide, and benzyl compounds, such as benzyl chloride or benzyl bromide.

Further suitable regulators are allyl compounds, such as, for example, allyl alcohol, functionalized allyl ethers, such as allyl ethoxylates, alkyl allyl ethers, or glyceryl monoallyl ethers.

Preferably, the regulators used are compounds which comprise sulfur in bonded form.

Compounds of this type are, for example, inorganic hydrogensulfites, disulfites and dithionites or organic sulfides, disulfides, polysulfides, sulfoxides and sulfones. These include di-n-butyl sulfide, di-n-octyl sulfide, diphenyl sulfide, thiodiglycol, ethylthio-ethanol, diisopropyl disulfide, di-n-butyl disulfide, di-n-hexyl disulfide, diacetyl disulfide, diethanol sulfide, di-t-butyl trisulfide, dimethyl sulfoxide, dialkyl sulfide, dialkyl disulfide and/or diaryl sulfide.

Particular preference is given to organic compounds which comprise sulfur in bonded form.

Preferably, compounds used as polymerization regulators are thiols (compounds which obtain sulfur in the form of SH groups, also referred to as mercaptans). As regulators, preference is given to mono-, bi- and polyfunctional mercaptans, mercapto alcohols and/or mercaptocarboxylic acids.

Examples of these compounds are allyl thioglycolates, ethyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercaptosuccinic acid, thioglycerol, thioacetic acid, thiourea and alkyl mercaptans, such as n-butyl mercaptan, n-hexyl mercaptan or n-dodecyl mercaptan.

Particularly preferred thiols are cysteine, 2-mercaptoethanol, 1,3-mercaptopropanol, 3-mercaptopropane-1,2-diol, thioglycerol, thiourea.

Examples of bifunctional regulators which comprise two sulfur atoms in bonded form are bifunctional thiols, such as, for example, dimercaptopropanesulfonic acid (sodium salt), dimercaptosuccinic acid, dimercapto-1-propanol, dimercaptoethane, dimercaptopropane, dimercaptobutane, dimercaptopentane, dimercaptohexane, ethylene glycol bisthioglycolates and butanediol bisthioglycolate.

Examples of polyfunctional regulators are compounds which comprise more than two sulfur atoms in bonded form. Examples thereof are trifunctional and/or tetrafunctional mercaptans.

Preferred trifunctional regulators are trifunctional mercaptans, such as, for example, trimethylpropane tris(2-mercaptoethanate), trimethylolpropane tris(3-mercapto-propionate), trimethylolpropane tris(4-mercaptobutanate), trimethylolpropane tris(5-mercaptopentanate), trimethylolpropane tris(6-mercaptohexanate), trimethylolpropane tris(2-mercaptoacetate), glyceryl thioglycolate, glyceryl thiopropionate, glyceryl thioethylate, glyceryl thiobutanate, 1,1,1-propanetriyl tris(mercaptoacetate), 1,1,1-propanetriyl tris(mercaptoethanate), 1,1,1-propanetriyl tris(mercaptopropionate), 1,1,1-propanetriyl tris(mercaptobutanate), 2-hydroxymethyl-2-methyl-1,3-propanediol tris(mercaptoacetate), 2-hydroxymethyl-2-methyl-1,3-propanediol tris(mercapto-ethanate), 2-hydroxymethyl-2-methyl-1,3-propanediol tris(mercapto-propionate), 2-hydroxymethyl-2-methyl-1,3-propanediol tris(mercaptobutanate).

Particularly preferred trifunctional regulators are glyceryl thioglycolate, trimethylolpropane tris(2-mercaptoacetate), 2-hydroxymethyl-2-methyl-1,3-propanediol tris(mercaptoacetate).

Preferred tetrafunctional mercaptans are pentaerythritol tetrakis(2-mercaptoacetate), pentaerythritol tetrakis(2-mercaptoethanate), pentaerythritol tetrakis(3-mercaptopropionate), pentaerythritol tetrakis(4-mercaptobutanate), pentaerythritol tetrakis(5-mercaptopentanate), pentaerythritol tetrakis(6-mercaptohexanate).

Further suitable polyfunctional regulators are polyfunctional regulators Si compounds of the formulae

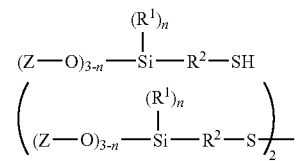

in which
n is a value from 0 to 2,
$R^1$ is a $C_1$-$C_{16}$-alkyl group or phenyl group,
$R^2$ is a $C_1$-$C_{18}$-alkyl group, the cyclohexyl group or phenyl group,
Z is a $C_1$-$C_{18}$-alkyl group, $C_2$-$C_{18}$-alkylene group or $C_2$-$C_{18}$-alkynyl group whose carbon atoms may be replaced by nonadjacent oxygen or halogen atoms, or is one of the groups

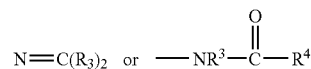

in which
$R_3$/$R^3$ is a $C_1$-$C_{12}$-alkyl group and
$R^4$ is a $C_1$-$C_{18}$-alkyl group.

All of the specified regulators can be used individually or in combination with one another.

Crosslinkers

In one embodiment of the invention, a crosslinker is used for the preparation of the polymers suitable for the use according to the invention. The meaning of the term "crosslinker" is known to the person skilled in the art. The crosslinker is preferably selected from compounds with at least two ethylenically unsaturated, nonconjugated double bonds suitable for the free-radical copolymerization per molecule.

Suitable crosslinkers c) are, for example, acrylic esters, methacrylic esters, allyl ethers or vinyl ethers of at least dihydric alcohols. The OH groups of the parent alcohols may here be completely or partially etherified or esterified; however, the crosslinkers comprise at least two ethylenically unsaturated groups.

Examples of the parent alcohols are dihydric alcohols, such as 1,2-ethanediol, 1,2-propanediol, 1,3-propanediol, 1,2-butanediol, 1,3-butanediol, 2,3-butanediol, 1,4-butanediol, but-2-ene-1,4-diol, 1,2-pentanediol, 1,5-pentanediol, 1,2-hexanediol, 1,6-hexanediol, 1,10-decanediol, 1,2-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, hydroxypivalic acid neopentyl glycol monoester, 2,2-bis(4-hydroxyphenyl)propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetra-hydrofurans with molecular weights of in each case 200 to 10 000.

Apart from the homopolymers of ethylene oxide and propylene oxide, it is also possible to use block copolymers of ethylene oxide or propylene oxide or copolymers which comprise ethylene oxide and propylene oxide groups in incorporated form.

Examples of parent alcohols having more than two OH groups are trimethylolpropane, glycerol, pentaerythritol, 1,2, 5-pentanetriol, 1,2,6-hexanetriol, triethoxycyanuric acid, sorbitan, sugars, such as sucrose, glucose, mannose. Preferred polyhydric alcohols in this connection are also di- and trisaccharides.

The polyhydric alcohols can of course also be used following reaction with ethylene oxide or propylene oxide as the corresponding ethoxylates or propoxylates, respectively. The polyhydric alcohols can also firstly be converted to the corresponding glycidyl ethers by reaction with epichlorohydrin.

Further suitable crosslinkers are the vinyl esters or the esters of monohydric, unsaturated alcohols with ethylenically unsaturated $C_3$- to $C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols with polybasic carboxylic acids, for example malonic acid, tartaric acid, trimellitic acid, phthalic acid, terephthalic acid, citric acid or succinic acid.

Further suitable crosslinkers are esters of unsaturated carboxylic acids with the above-described polyhydric alcohols, for example oleic acid, crotonic acid, cinnamic acid or 10-undecenoic acid.

Suitable crosslinkers are, furthermore, straight-chain or branched, linear or cyclic, aliphatic or aromatic hydrocarbons which have at least two double bonds which, in the case of aliphatic hydrocarbons, must not be conjugated, e.g. divinylbenzene, divinyltoluene, 1,7-octadiene, 1,9-decadiene, 4-vinyl-1-cyclohexene, trivinylcyclo-hexane or polybutadienes with molecular weights of from 200 to 20 000.

Also suitable as crosslinkers are the amides of (meth) acrylic acid, itaconic acid and maleic acid, and N-allylamines of at least difunctional amines. Such amines are, for example, 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Likewise suitable are the amides of allylamine and unsaturated carboxylic acids, such as acrylic acid, methacrylic acid, itaconic acid, maleic acid, or at least dibasic carboxylic acids, as have been described above.

Also suitable as crosslinkers are triallylamine and triallylmonoalkylammonium salts, e.g. triallylmethylammonium chloride or methyl sulfate.

Also suitable are N-vinyl compounds of urea derivatives, at least difunctional amides, cyanurates or urethanes, for example of urea, ethyleneurea, propyleneurea or tartardiamide, e.g. N,N'-divinylethyleneurea or N,N'-divinylpropyleneurea.

Also suitable are alkylenebisacrylamides, such as methylenebisacrylamide and N,N'-(2,2)butane and 1,1'-bis(3,3'-vinylbenzimidazolith-2-one)-1,4-butane.

Other suitable crosslinkers are, for example, alkylene glycol di(meth)acrylates, such as ethylene glycol diacrylate, ethylene glycol dimethacrylate, tetraethylene glycol acrylate, tetraethylene glycol dimethacrylate, diethylene glycol acrylate, diethylene glycol methacrylate, vinyl acrylate, allyl acrylate, allyl methacrylate, divinyldioxane, penta-erythritol allyl ether, and mixtures of these crosslinkers.

Further suitable crosslinkers are divinyldioxane, tetraallylsilane or tetravinylsilane.

Crosslinkers that are particularly preferably used are methylenebisacrylamide, triallylamine, triallylalkylammonium salts, divinylimidazole, pentaerythritol triallyl ether, N,N'-divinylethyleneurea, reaction products of polyhydric alcohols with acrylic acid or methacrylic acid, methacrylic acid esters and acrylic acid esters of polyalkylene oxides or polyhydric alcohols which have been reacted with ethylene oxide and/or propylene oxide and/or epichlorohydrin.

Very particularly preferred crosslinkers are pentaerythritol triallyl ether, methylenebisacrylamide, N,N'-divinylethyleneurea, triallylamine and triallylmonoalkylammonium salts, and acrylic acid esters of ethylene glycol, butanediol, trimethylolpropane or glycerol or acrylic acid esters of glycol, butanediol, trimethylolpropane or glycerol reacted with ethylene oxide and/or epichlorohydrin. Pentaerythritol triallyl ether is most preferred.

It is of course also possible to use mixtures of the above-mentioned compounds. The crosslinker is preferably soluble in the reaction medium. If the solubility of the crosslinker in the reaction medium is low, then it can be dissolved in a monomer or in a monomer mixture, or else be metered in dissolved in a solvent which mixes with the reaction medium. Particular preference is given to those crosslinkers which are soluble in the monomer mixture.

If crosslinkers are used for the polymerization, then in amounts of at least 0.01% by weight, preferably at least 0.05% by weight, particularly preferably at least 0.1% by weight and at most 5% by weight, preferably at most 2% by weight and particularly preferably at most 1% by weight, based on the total amount of the monomers a) to c) to be polymerized.

In a particularly preferred embodiment of the invention, pentaerythritol triallyl ether is used in an amount of from 0.1% by weight to 0.7% by weight, most preferably in an amount of from 0.3% by weight to 0.6% by weight.

The % by weight amount of the crosslinker refers to the total amount of the monomers a) to c) used for the preparation of the polymer.

However, in one preferred embodiment, no crosslinker is used for the preparation of the polymers.

K Values

The K values of the polymers suitable for the use according to the invention are preferably in the range from 20 to 60, particularly preferably 30 to 55 and in particular 40 to 50.

If the monomer b) used for the polymerization consists to at least 70 mol %, preferably to at least 80 mol % and in particular to at least 90 mol %, of methacrylic acid, then the K values of polymers suitable for the use according to the invention are particularly preferably in the range from 20 to 30.

The method for determining the K values is described below.

Hair Cosmetic Preparations

The polymer suitable for the use according to the invention is present in the cosmetic compositions in an amount of from 0.01 to 10% by weight, preferably from 0.05 to 1% by weight, particularly preferably 0.1 to 0.8% by weight, based on the weight of the composition.

In a preferred embodiment of the invention, the shampoos and haircare compositions according to the invention further comprise, in addition to the cationic polymer, at least one surfactant.

In a further preferred embodiment of the invention, the shampoos and haircare compositions according to the invention comprise, besides the cationic polymer, also at least one oil and/or fat phase and a surfactant.

Surfactants

Surfactants which can be used are anionic, cationic, nonionic and/or amphoteric surfactants.

Advantageous washing-active anionic surfactants for the purposes of the present invention are acylamino acids and salts thereof, such as acyl glutamates, in particular sodium acyl glutamate sarcosinates, for example myristoyl sarcosine, TEA-lauroyl sarcosinate, sodium lauroyl sarcosinate and sodium cocoyl sarcosinate, sulfonic acids and salts thereof, such as acyl isethionates, for example sodium or ammonium cocoyl isethionate sulfosuccinates, for example dioctyl sodium sulfosuccinate, disodium laureth sulfosuccinate, disodium lauryl sulfosuccinate and disodium undecyleneamido MEA sulfosuccinate, disodium PEG-5 lauryl citrate sulfosuccinate and derivatives, alkyl ether sulfates, for example sodium, ammonium, magnesium, MIPA, TIPA laureth sulfate, sodium myreth sulfate and sodium $C_{12-13}$ pareth sulfate, alkyl sulfates, for example sodium, ammonium and TEA lauryl sulfate.

Further advantageous anionic surfactants are taurates, for example sodium lauroyl taurate and sodium methyl cocoyl taurate, ether carboxylic acids, for example sodium laureth-13 carboxylate and sodium PEG-6 cocamide carboxylate, sodium PEG-7 olive oil carboxylate phosphoric acid esters and salts, such as, for example, DEA oleth-10 phosphate and dilaureth-4 phosphate, alkylsulfonates, for example sodium cocomonoglyceride sulfate, sodium $C_{12-14}$ olefinsulfonate, sodium lauryl sulfoacetate and magnesium PEG-3 cocamide sulfate, acyl glutamates, such as di-TEA palmitoyl aspartate and sodium caprylic/capric glutamate, acyl peptides, for example palmitoyl hydrolyzed milk protein, sodium cocoyl hydrolyzed soya protein and sodium/potassium cocoyl hydrolyzed collagen, and carboxylic acids and derivatives, such as, for example, lauric acid, aluminum stearate, magnesium alkanolate and zinc undecylenate, ester carboxylic acids, for example calcium stearoyl lactylate, laureth-6 citrate and sodium PEG-4 lauramide carboxylate alkylarylsulfonates.

Advantageous washing-active cationic surfactants for the purposes of the present invention are quaternary surfactants. Quaternary surfactants comprise at least one N atom which is covalently bonded to four alkyl or aryl groups. Alkylbetaine, alkylamidopropylbetaine and alkylamidopropylhydroxysultaine, for example, are advantageous. Further advantageous cationic surfactants for the purposes of the present invention are also alkylamines, alkylimidazoles and ethoxylated amines and in particular salts thereof.

Advantageous washing-active amphoteric surfactants for the purposes of the present invention are acyl/dialkylethylenediamines, for example sodium acyl amphoacetate, disodium acyl amphodipropionate, disodium alkyl amphodiacetate, sodium acyl amphohydroxypropylsulfonate, disodium acyl amphodiacetate, sodium acyl amphopropionate, and N-coconut-fatty acid-amidoethyl-N-hydroxyethyl glycinate sodium salts.

Further advantageous amphoteric surfactants are N-alkylamino acids, for example aminopropylalkylglutamide, alkylaminopropionic acid, sodium alkylimidodipropionate and lauroamphocarboxyglycinate.

Advantageous washing-active nonionic surfactants for the purposes of the present invention are alkanolamides, such as cocamides MEA/DEA/MIPA, esters which are formed by esterification of carboxylic acids with ethylene oxide, glycerol, sorbitan or other alcohols, ethers, for example ethoxylated alcohols, ethoxylated lanolin, ethoxylated polysiloxanes, propoxylated POE ethers, alkyl polyglycosides, such as lauryl glucoside, decyl glycoside and cocoglycoside, glycosides with an HLB value of at least 20 (e.g. Belsil®SPG 128V (Wacker)).

Further advantageous nonionic surfactants are alcohols and amine oxides, such as cocoamidopropylamine oxide.

Preferred anionic, amphoteric and nonionic shampoo surfactants are specified, for example, in "Kosmetik and Hygiene von Kopf bis Fuß" [Cosmetics and hygiene from head to toe], Ed. W. Umbach, 3rd Edition, Wiley-VCH, 2004, pp. 131-134, to which reference is made at this point in its entirety.

Among the alkyl ether sulfates, sodium alkyl ether sulfates based on di- or triethoxylated lauryl and myristyl alcohol, in particular, are preferred. They surpass the alkyl sulfates to a considerable degree with regard to the insensitivity toward water hardness, the ability to be thickened, low-temperature solubility and, in particular, skin and mucosa compatibility. They can also be used as the sole washing raw materials for shampoos. Lauryl ether sulfate has better foaming properties than myristyl ether sulfate, but is inferior to this in terms of mildness.

Alkyl ether carboxylates with average and particularly with relatively high belong to the mildest surfactants overall, but exhibit a poor foaming and viscosity behavior. They are often used in combination with alkyl ether sulfates and amphoteric surfactants in hair-washing compositions.

Sulfosuccinic acid esters (sulfosuccinates) are mild and readily foaming surfactants, but, on account of their poor ability to be thickened, are preferably only used together with other anionic and amphoteric surfactants and, on account of their low hydrolysis stability, are preferably only used in neutral or well buffered products. Amidopropylbetaines are virtually insignificant as sole washing raw materials since their foaming behavior and their ability to be thickened are only moderately pronounced. By contrast, these surfactants have excellent skin and eye mucosa compatibility. In combination with anionic surfactants, their mildness can be synergistically improved. Preference is given to the use of cocamidopropylbetaine. Amphoacetates/amphodiacetates have, as amphoteric surfactants, very good skin and mucosa compatibility and can have a hair-conditioning effect and/or increase the care effect of additives. They are used similarly to the betaines for optimizing alkyl ether sulfate formulations. Sodium cocoamphoacetate and disodium cocoamphodiacetate are most preferred.

Alkyl polyglycosides are nonionic washing raw materials. They are mild, have good universal properties, but are weakly foaming. For this reason, they are preferably used in combination with anionic surfactants.

Sorbitan esters likewise belong to the nonionic washing raw materials. On account of their excellent mildness, they are preferably used in baby shampoos. As low-foamers, they are preferably used in combination with anionic surfactants.

It is advantageous to choose the washing-active surfactant(s) from the group of surfactants which have an HLB value of more than 25, those which have an HLB value of more than 35 being particularly advantageous.

According to the invention, it is advantageous if one or more of these surfactants is used in a concentration from 1 to 30% by weight, preferably in a concentration of from 5 to 25% by weight and very particularly preferably in a concentration of from 10 to 20% by weight, in each case based on the total weight of the composition.

Polysorbates

Washing-active agents which can also advantageously be incorporated into the compositions according to the invention are polysorbates.

Polysorbates advantageous for the purposes of the invention are, for example, polyoxyethylene(20) sorbitan monolaurate (Tween®20, CAS No. 9005-64-5)

polyoxyethylene(4) sorbitan monolaurate (Tween®21, CAS No. 9005-64-5)

polyoxyethylene(4) sorbitan monostearate (Tween®61, CAS No. 9005-67-8)

polyoxyethylene(20) sorbitan tristearate (Tween®65, CAS No. 9005-71-4)

polyoxyethylene(20) sorbitan monooleate (Tween®60, CAS No. 9005-65-6)

polyoxyethylene(5) sorbitan monooleate (Tween®81, CAS No. 9005-65-5)

polyoxyethylene(20) sorbitan trioleate (Tween®85, CAS No. 9005-70-3).

Polyoxyethylene(20) sorbitan monopalmitate (Tween®40, CAS No. 9005-66-7) and polyoxyethylene(20) sorbitan monostearate (Tween®60, CAS No. 9005-67-8)

are particularly advantageous.

The polysorbates are advantageously used in a concentration of from 0.1 to 5% by weight and in particular in a concentration of from 1.5 to 2.5% by weight, based on the total weight of the composition, individually or as a mixture of two or more polysorbates.

Conditioning Agents

In a preferred embodiment, the haircare compositions and shampoos according to the invention comprise further conditioning agents (conditioners).

Conditioning agents preferred according to the invention are, for example, the compounds which are listed in the International Cosmetic Ingredient Dictionary and Handbook (Volume 4, Editors: R. C. Pepe, J. A. Wenninger, G. N. McEwen, The Cosmetic, Toiletry, and Fragrance Association, 9th edition, 2002) under Section 4 under the keywords Hair Conditioning Agents, Humectants, Skin-Conditioning Agents, Skin-Conditioning Agents-Emollient, Skin-Conditioning Agents-Humectant, Skin-Conditioning Agents-Miscellaneous, Skin-Conditioning Agents-Occlusive and Skin Protectants, and also the compounds listed in EP-A 934 956 (pp. 11-13) under "water soluble conditioning agent" and "oil soluble conditioning agent". Reference is made to these literature references in their entirety. Further advantageous conditioning agents are, for example, the compounds referred to in accordance with INCI as Polyquaternium (in particular Polyquaternium-1 to Polyquaternium-74, see also Table 1 below).

Suitable conditioning agents include, for example, also polymeric quaternary ammonium compounds, cationic cellulose derivatives, chitosan derivatives, starch derivatives, maltodextrin derivatives and polysaccharide derivatives, and also quaternary protein hydrolyzates and quaternary silicone derivatives. Conditioning agents advantageous according to the invention can be selected here from among the compounds shown in Table 1 below.

TABLE 1

Conditioning agents to be used advantageously

| INCI Name | CAS Number | Polymer type | Example (trade name) |
|---|---|---|---|
| Polyquaternium-2 | CAS 63451-27-4 | Urea, N,N'-bis[3-(dimethyl-amino)propyl], polymer with 1,1'-oxybis(2-chloroethane) | Mirapol ® A-15 |
| Polyquaternium-5 | CAS 26006-22-4 | Acrylamide, β-methacryloxyethyl-triethylammonium methosulfate | |
| Polyquaternium-6 | CAS 26062-79-3 | N,N-Dimethyl-N-2-propenyl-2-propenaminium chloride | Merquat ® 100 |
| Polyquaternium-7 | CAS 26590-05-6 | N,N-Dimethyl-N-2-propenyl-2-propenaminium chloride, 2-propenamide | Merquat ® S |
| Polyquaternium-10 | CAS 53568-66-4, 55353-19-0, 54351-50-7, 68610-92-4, 81859-24-7 | Quaternary ammonium salt of hydroxyethylcellulose | Celquat ® SC-230M, Polymer JR 400 |
| Polyquaternium-11 | CAS 53633-54-8 | Vinylpyrrolidone/dimethylaminoethyl methacrylate copolymer/diethyl sulfate reaction product | Gafquat ® 755N |
| Polyquaternium-16 | CAS 29297-55-0 | Vinylpyrrolidone/vinylimidazolium methochloride copolymer | Luviquat ® HM552 |
| Polyquaternium-17 | CAS 90624-75-2 | | Mirapol ® AD-1 |
| Polyquaternium-19 | CAS 110736-85-1 | Quaternized water-soluble polyvinyl alcohol | |
| Polyquaternium-20 | CAS 110736-86-2 | Quaternized polyvinyl octadecyl ether dispersible in water | |
| Polyquaternium-21 | | Polysiloxane-polydimethyldimethyl-ammonium acetate copolymer | Abil ® B 9905 |
| Polyquaternium-22 | CAS 53694-17-0 | Dimethyldiallylammonium chloride/acrylic acid copolymer | Merquat ® 280 |

TABLE 1-continued

Conditioning agents to be used advantageously

| INCI Name | CAS Number | Polymer type | Example (trade name) |
|---|---|---|---|
| Polyquaternium-24 | CAS 107987-23-5 | Polymeric quaternary ammonium salt of hydroxyethylcellulose | Quartisoft ® LM-200 |
| Polyquaternium-28 | CAS 131954-48-8 | Vinylpyrrolidone/methacrylamido-propyltrimethylammonium chloride copolymer | Gafquat ® HS-100 |
| Polyquaternium-29 | CAS 92091-36-6, 148880-30-2 | Chitosan which has been reacted with propylene oxide and quaternized with epichlorohydrin | Lexquat ® CH |
| Polyquaternium-31 | CAS 136505-02-7, 139767-67-7 | Polymeric, quaternary ammonium salt which is prepared by reacting DMAPA acrylates/acrylic acid/acrylonitrogens copolymer and diethyl sulfate | Hypan ® QT 100 |
| Polyquaternium-32 | CAS 35429-19-7 | N,N,N-trimethyl-2-([82-methyl-1-oxo-2-propenyl)oxy]ethaneaminium chloride, polymer with 2-propenamide | |
| Polyquaternium-37 | CAS 26161-33-1 | | |
| Polyquaternium-44 | | Copolymeric quaternary ammonium salt of vinylpyrrolidone and quaternized imidazoline | |

Further conditioning agents advantageous according to the invention are cellulose derivatives, in particular Polyquaternium-10 and Polyquaternium-67 (e.g. Ucare® polymer grades, SoftCAT® polymer grades (Dow Chemical)) and quaternized guar gum derivatives, in particular guar hydroxypropylammonium chloride (e.g. Jaguar® Excel, Jaguar®C 162, Jaguar®C-14S or C-13S (Rhodia), CAS 65497-29-2, CAS 39421-75-5).

Nonionic poly-N-vinylpyrrolidone/polyvinyl acetate copolymers (e.g. Luviskol®VA 64 (BASF)), anionic acrylate copolymers (e.g. Luviflex®Soft (BASF)), and/or amphoteric amide/acrylate/methacrylate copolymers (e.g. Amphomer® (National Starch)) can also be used advantageously as conditioning agents.

Rheology Modifiers

Suitable rheology modifiers are primarily thickeners.

Thickeners suitable for shampoos and haircare compositions are specified in "Kosmetik and Hygiene von Kopf bis Fuß" [Cosmetics and hygiene from head to toe], Ed. W. Umbach, 3rd Edition, Wiley-VCH, 2004, pp. 235-236, to which reference is made at this point in its entirety.

Thickeners which bring about a viscosity-increasing effect as a result of an enlargement of the surfactant micelles or as a result of a swelling of the water phase originate in chemical terms from very different classes of substances.

Suitable thickeners for the compositions according to the invention are crosslinked polyacrylic acids and derivatives thereof, polysaccharides, such as xanthan gum, guar guar, agar agar, alginates or tyloses, cellulose derivatives, e.g. carboxymethylcellulose or hydroxycarboxymethylcellulose, and also relatively high molecular weight polyethylene glycol mono- and diesters of fatty acids, fatty alcohols, monoglycerides and fatty acids, polyvinyl alcohol and polyvinylpyrrolidone.

Suitable thickeners are also polyacrylates, such Carbopol® (Noveon), Ultrez® (Noveon), Luvigel® EM (BASF), Capigel®98 (Seppic), Synthalene® (Sigma), the Aculyn® grades from Rohm and Haas, such as Aculyn® 22 (copolymer of acrylates and methacrylic acid ethoxylates with stearyl radical (20 ethylene oxide (EO) units)) and Aculyn® 28 (copolymer of acrylates and methacrylic acid ethoxylates with behenyl radical (25 EO units)).

Suitable thickeners are furthermore, for example, aerosol grades (hydrophilic silicas), polyacrylamides, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with a narrowed homolog distribution or alkyl oligoglucosides, and also electrolytes such as sodium chloride and ammonium chloride.

Particularly preferred thickeners for producing gels are Ultrez®21, Aculyn®28, Luvigel® EM and Capigel®98.

Particularly in the case of relatively high-concentration shampoo formulations, it is also possible, for regulating the consistency, to add substances which reduce the viscosity of the formulation, such as, for example, propylene glycol or glycerol. These substances only influence the product properties slightly.

Preservatives

The compositions according to the invention can advantageously comprise one or more preservatives. Products with high water contents, for example, shampoos, have to be reliably protected against the build-up of germs. The most important preservatives used for this purpose are urea condensates, p-hydroxybenzoic acid esters, the combination of phenoxyethanol with methyldibromoglutaronitrile and acid preservatives containing benzoic acid, salicylic acid and sorbic acid.

Shampoo concentrates with high fractions of surfactants or polyols and low water contents can also be formulated without preservatives.

Advantageous preservatives within the context of the present invention are, for example, formaldehyde donors (such as, for example, DMDM hydantoin, which is commercially available, for example, under the trade name Glydant® (Lonza)), iodopropyl butylcarbamates (e.g. Glycacil-L®, Glycacil-S® (Lonza), Dekaben®LMB (Jan Dekker)), parabens (p-hydroxybenzoic acid alkyl esters, such as, for example, methyl, ethyl, propyl and/or butylparaben), dehydroacetic acid (Euxyl® K 702 (Schülke & Mayr), phenoxyethanol, ethanol, benzoic acid. So-called preservation aids, such as, for example, octoxyglycerol, glycine, soya etc., are also advantageously used. The table below gives an overview of customary preservatives:

| | |
|---|---|
| E200 | Sorbic acid |
| E201 | Sodium sorbate |
| E202 | Potassium sorbate |
| E203 | Calcium sorbate |
| E210 | Benzoic acid |
| E211 | Sodium benzoate |
| E212 | Potassium benzoate |
| E213 | Calcium benzoate |
| E214 | Ethyl p-hydroxybenzoate |
| E215 | Ethyl p-hydroxybenzoate Na salt |
| E216 | n-Propyl p-hydroxybenzoate |
| E217 | n-Propyl p-hydroxybenzoate Na salt |
| E218 | Methyl p-hydroxybenzoate |
| E219 | Methyl p-hydroxybenzoate Na salt |
| E220 | Sulfur dioxide |
| E221 | Sodium sulfite |
| E222 | Sodium hydrogen sulfite |
| E223 | Sodium disulfite |
| E224 | Potassium disulfite |
| E226 | Calcium sulfite |
| E227 | Calcium hydrogen sulfite |
| E228 | Potassium hydrogen sulfite |
| E230 | Biphenyl (diphenyl) |
| E231 | Orthophenylphenol |
| E232 | Sodium orthophenylphenolate |
| E233 | Thiabendazole |
| E235 | Natamycin |
| E236 | Formic acid |
| E237 | Sodium formate |
| E238 | Calcium formate |
| E239 | Hexamethylenetetramine |
| E249 | Potassium nitrite |
| E250 | Sodium nitrite |
| E251 | Sodium nitrate |
| E252 | Potassium nitrate |
| E280 | Propionic acid |
| E281 | Sodium propionate |
| E282 | Calcium propionate |
| E283 | Potassium propionate |
| E290 | Carbon dioxide |

Also advantageous are preservatives or preservation aids customary in cosmetics, such as dibromodicyanobutane (2-bromo-2-bromomethylglutarodinitrile), phenoxyethanol, 3-iodo-2-propynyl butylcarbamate, 2-bromo-2-nitropropane-1,3-diol, imidazolidinylurea, 5-chloro-2-methyl-4-isothiazolin-3-one, 2-chloroacetamide, benzalconium chloride, benzyl alcohol, salicylic acid and salicylates. It is particularly preferred if the preservatives used are iodopropyl butylcarbamates, parabens (methyl, ethyl, propyl and/or butyl paraben) and/or phenoxyethanol.

Complexing agents: Since the raw materials and also the shampoos themselves are prepared predominantly in steel apparatuses, the end products can comprise iron (ions) in trace amounts. In order to prevent these impurities adversely affecting the product quality via reactions with dyes and perfume oil constituents, complexing agents, such as salts of ethylenediaminetetraacetic acid, of nitrilotriacetic acid, of iminodisuccinic acid or phosphates are added.

UV photoprotective filters: In order to stabilize the ingredients present in the compositions according to the invention, such as, for example, dyes and perfume oils, against changes as a result of UV light, UV photoprotective filters, such as, for example, benzophenone derivatives, can be incorporated. All cosmetically acceptable UV photoprotective filters are suitable for this purpose.

Antioxidants: A content of antioxidants is generally preferred. According to the invention, antioxidants which can be used are all antioxidants which are customary or suitable for cosmetic applications. The antioxidants are advantageously selected from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, γ-lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdine, EDTA, EGTA and derivatives thereof, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutine, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

The amount of the abovementioned antioxidants (one or more compounds) in the compositions is preferably 0.001 to 30% by weight, particularly preferably 0.05 to 20% by weight, in particular 0.1 to 10% by weight, based on the total weight of the composition.

If vitamin E and/or derivatives thereof are the antioxidant or the antioxidants, it is advantageous to provide these in concentrations of from 0.001 to 10% by weight, based on the total weight of the composition.

If vitamin A or vitamin A derivatives, or carotenes or derivatives thereof are the antioxidant or the antioxidants, it is advantageous to provide these in concentrations of from 0.001 to 10% by weight, based on the total weight of the composition.

Buffers: Buffers ensure the pH stability of the compositions. By and large, citrate, lactate and phosphate buffers are used.

Solubility promoters: They are used in order to dissolve care oils or perfume oils to give clear solutions and also to maintain clear solutions at low temperature. The most common solubility promoters are ethoxylated nonionic surfactants, e.g. hydrogenated and ethoxylated castor oils.

Antimicrobial agents: Furthermore, antimicrobial agents can also be used. These include, in general, all suitable preservatives with a specific effect toward Gram-positive bacteria, e.g. triclosan (2,4,4'-trichloro-2'-hydroxydiphenyl ether), chlorhexidine (1,1'-hexamethylenebis[5-(4-chlorophenyl)

biguanide), and TTC (3,4,4'-trichlorocarbanilide). Quaternary ammonium compounds are in principle likewise suitable and are preferably used for disinfecting soaps and washing lotions. Numerous fragrances also have antimicrobial properties. Also, a large number of essential oils or their characteristic ingredients, such as, for example, oil of cloves (eugenol), mint oil (menthol) or thyme oil (thymol), exhibit marked antimicrobial effectiveness.

The antibacterially effective substances are generally used in concentrations of from about 0.1 to 0.3% by weight.

Dispersants: If insoluble active ingredients, e.g. antidandruff active ingredients or silicone oils, are to be dispersed or kept permanently in suspension in the compositions according to the invention, dispersants and thickeners, such as, for example, magnesium aluminum silicates, bentonites, fatty acyl derivatives, polyvinylpyrrolidone or hydrocolloids, e.g. xanthan gum or carbomers, have to be used. According to the invention, preservatives in a total concentration of at most 2% by weight, preferably at most 1.5% by weight and particularly preferably at most 1% by weight, based on the total weight of the composition, are present.

Oils, Fats and Waxes

The compositions according to the invention preferably comprise oils, fats and/or waxes.

Constituents of the oil phase and/or fat phase of the composition according to the invention are advantageously selected from the group of lecithins and fatty acid triglycerides, namely the triglycerol esters of saturated and/or unsaturated, branched and/or unbranched alkanecarboxylic acids of chain length from 8 to 24, in particular 12 to 18 carbon atoms. The fatty acid triglycerides can, for example, advantageously be selected from the group of synthetic, semisynthetic and natural oils, such as, for example, olive oil, sunflower oil, soya oil, peanut oil, rapeseed oil, almond oil, palm oil, coconut oil, castor oil, wheatgerm oil, grapeseed oil, safflower oil, evening primrose oil, macadamia nut oil and the like. Further polar oil components can be selected from the group of esters of saturated and/or unsaturated, branched and/or unbranched alkanecarboxylic acids of chain length from 3 to 30 carbon atoms with saturated and/or unsaturated, branched and/or unbranched alcohols of chain length from 3 to 30 carbon atoms, and also from the group of esters of aromatic carboxylic acids with saturated and/or unsaturated, branched and/or unbranched alcohols of chain length from 3 to 30 carbon atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate dicaprylyl carbonate (Cetiol CC) and cocoglycerides (Myritol 331), butylene glycol dicaprylate/dicaprate and dibutyl adipate, and also synthetic, semisynthetic and natural mixtures of such esters, such as, for example, jojoba oil.

Furthermore, one or more oil components can advantageously be selected from the group of branched and unbranched hydrocarbons and hydrocarbon waxes, silicone oils, dialkyl ethers, the group of saturated or unsaturated, branched or unbranched alcohols.

Any desired mixtures of such oil and wax components are also to be used advantageously within the context of the present invention. If appropriate, it may also be advantageous to use waxes, for example cetyl palmitate, as the sole lipid component of the oil phase.

According to the invention, the oil component is advantageously selected from the group 2-ethylhexyl isostearate, octyldodecanol, isotridecyl isononanoate, isoeicosane, 2-ethylhexyl cocoate, C12-15-alkyl benzoate, capryl-capric acid triglyceride, dicaprylyl ether.

Mixtures of C12-C15-alkyl benzoate and 2-ethylhexyl isostearate, mixtures of C12-15-alkylbenzoate and isotridecyl isononanoate, and also mixtures of C12-15-alkylbenzoate, 2-ethylhexyl isostearate and isotridecyl isononanoate are advantageous according to the invention.

According to the invention, the oils with a polarity of from 5 to 50 mN/m used are particularly preferably fatty acid triglycerides, in particular soya oil and/or almond oil. Of the hydrocarbons, paraffin oil, squalane, squalene and in particular (if appropriate hydrogenated) polyisobutenes are to be used advantageously within the context of the present invention.

In addition, the oil phase can advantageously be selected from the group of Guerbet alcohols. Guerbet alcohols are formed according to the reaction equation

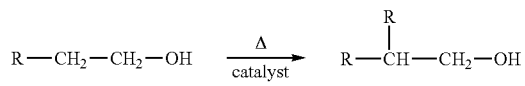

by oxidation of an alcohol to give an aldehyde, by aldol condensation of the aldehyde, elimination of water from the aldol and hydrogenation of the allyl aldehyde. Guerbet alcohols are liquid even at low temperatures and cause virtually no skin irritations. They can advantageously be used as fatting, superfatting and also refatting constituents in cosmetic compositions.

The use of Guerbet alcohols in cosmetics is known per se. Such species are then in most cases characterized by the structure

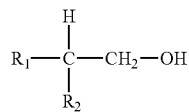

Here, $R_1$ and $R_2$ are generally unbranched alkyl radicals.

According to the invention, the Guerbet alcohol or alcohols is/are advantageously selected from the group where
$R_1$=propyl, butyl, pentyl, hexyl, heptyl or octyl and
$R_2$=hexyl, heptyl, octyl, nonyl, decyl, undecyl, dodecyl, tridecyl or tetradecyl.

Guerbet alcohols preferred according to the invention are 2-butyloctanol (commercially available, for example, as Isofol® 12 (Condea)) and 2-hexyldecanol (commercially available, for example as Isofol® 16 (Condea)).

Mixtures of Guerbet alcohols according to the invention are also to be used advantageously according to the invention, such as, for example, mixtures of 2-butyloctanol and 2-hexyldecanol (commercially available, for example, as Isofol® 14 (Condea)).

Any desired mixtures of such oil and wax components are also to be used advantageously within the context of the present invention.

Among the polyolefins, polydecenes are the preferred substances.

Advantageously, the oil component can also have a content of cyclic or linear silicone oils or consist entirely of such oils, although it is preferred to use an additional content of other oil phase components apart from the silicone oil or the silicone oils.

Low molecular weight silicones or silicone oils are generally defined by the following general formula

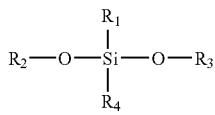

Higher molecular weight silicones or silicone oils are generally defined by the following general formula

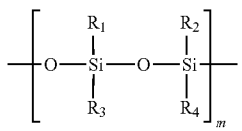

where the silicon atoms may be substituted by identical or different alkyl radicals and/or aryl radicals, which are shown here in general terms by the radicals $R_1$ to $R_4$. However, the number of different radicals is not necessarily limited to up to 4. m can here assume values from 2 to 200 000.

Cyclic silicones to be used advantageously according to the invention are generally defined by the following general formula

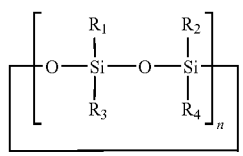

where the silicon atoms may be substituted by identical or different alkyl radicals and/or aryl radicals, which are shown here in general terms by the radicals $R_1$ to $R_4$. However, the number of different radicals is not necessarily limited to up to 4. n can here assume values from 3/2 to 20. Fractional values for n take into consideration that odd numbers of siloxyl groups may be present in the cycle.

Phenyltrimethicone is advantageously selected as silicone oil. Other silicone oils, for example dimethicone, hexamethylcyclotrisiloxane, phenyldimethicone, cyclomethicone (e.g. decamethylcyclopentasiloxane), hexamethylcyclotrisiloxane, polydimethylsiloxane, poly(methylphenylsiloxane), cetyldimethicone, behenoxydimethicone, are also to be used advantageously within the context of the present invention. Mixtures of cyclomethicone and isotridecyl isononanoate, and also those of cyclomethicone and 2-ethylhexyl isostearate are also advantageous.

However, it is also advantageous to select silicone oils of similar constitution to that of the abovementioned compounds whose organic side chains are derivatized, for example polyethoxylated and/or polypropoxylated. These include, for example, polysiloxane polyalkyl-polyether copolymers, such as, for example, cetyl-dimethicone copolyol.

Cyclomethicone (octamethylcyclotetrasiloxane) is advantageously used as silicone oil to be used according to the invention.

Fat and/or wax components to be used advantageously according to the invention can be selected from the group of vegetable waxes, animal waxes, mineral waxes and petrochemical waxes. For example, candelilla wax, carnauba wax, Japan wax, esparto grass wax, cork wax, guaruma wax, rice germ oil wax, sugarcane wax, berry wax, ouricury wax, montan wax, jojoba wax, shea butter, beeswax, shellac wax, spermaceti, lanolin (wool wax), uropygial grease, ceresine, ozokerite (earth wax), paraffin waxes and microwaxes are advantageous.

Further advantageous fat and/or wax components are chemically modified waxes and synthetic waxes, such as, for example, Syncrowax®HRC (glyceryl tribehenate), and Syncrowax®AW 1 C($C_{18-36}$-fatty acid), and also montan ester waxes, sasol waxes, hydrogenated jojoba waxes, synthetic or modified beeswaxes (e.g. dimethicone copolyol beeswax and/or $C_{30-50}$-alkyl beeswax), cetyl ricinoleates, such as, for example, Tegosoft®CR, polyalkylene waxes, polyethylene glycol waxes, but also chemically modified fats, such as, for example, hydrogenated vegetable oils (for example hydrogenated castor oil and/or hydrogenated coconut fatty glycerides), triglycerides, such as, for example, hydrogenated soy glyceride, trihydroxystearin, fatty acids, fatty acid esters and glycol esters, such as, for example, $C_{20-40}$-alkyl stearate, $C_{20-40}$-alkyl hydroxystearoylstearate and/or glycol montanate. Also advantageous are furthermore certain organosilicon compounds which have similar physical properties to the specified fat and/or wax components, such as, for example, stearoxytrimethyl-silane.

According to the invention, the fat and/or wax components can either be used individually or else as a mixture in the compositions.

Any desired mixtures of such oil and wax components are also to be used advantageously within the context of the present invention.

The oil phase is advantageously selected from the group 2-ethylhexyl isostearate, octyldodecanol, isotridecyl isononanoate, butylene glycol dicaprylate/dicaprate, 2-ethylhexyl cocoate, $C_{12-15}$-alkyl benzoate, caprylic/capric acid triglyceride, dicaprylyl ether.

Mixtures of octyldodecanol, caprylic/capric acid triglyceride, dicaprylyl ether, dicaprylyl carbonate, coco glycerides or mixtures of $C_{12-15}$-alkyl benzoate and 2-ethylhexyl isostearate, mixtures of $C_{12-15}$-alkyl benzoate, and butylene glycol dicaprylate/dicaprate, and also mixtures of $C_{12-15}$-alkyl benzoate, 2-ethylhexyl isostearate and isotridecyl isononanoate are particularly advantageous.

Of the hydrocarbons, paraffin oil, cycloparaffin, squalane, squalene, hydrogenated polyisobutene and polydecene are to be used advantageously within the context of the present invention.

The oil component is also advantageously selected from the group of phospholipids. The phospholipids are phosphoric acid esters of acylated glycerols. Of the greatest importance among the phosphatidylcholines are, for example, the lecithins, which are characterized by the general structure

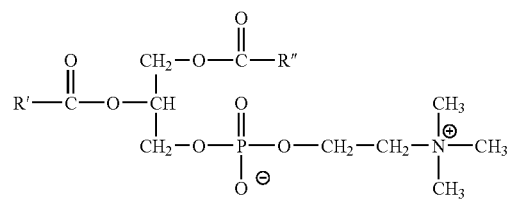

where R' and R" are typically unbranched aliphatic radicals having 15 or 17 carbon atoms and up to 4 cis double bonds.

According to the invention, paraffin oil advantageous according to the invention that can be used is Merkur White Oil Pharma 40 from Merkur Vaseline, Shell Ondina® 917, Shell Ondina® 927, Shell Oil 4222, Shell Ondina®933 from Shell & DEA Oil, Pionier® 6301 S, Pionier® 2071 (Hansen & Rosenthal).

Suitable cosmetically compatible oil and fat components are described in Karl-Heinz Schrader, Grundlagen und Rezepturen der Kosmetika [Fundamentals and Formulations of Cosmetics], 2nd edition, Verlag Hüthig, Heidelberg, pp. 319-355, to which reference is made here in its entirety.

The content of further oils, fats and waxes is at most 50% by weight, preferably 30% by weight, further preferably at most 20% by weight, based on the total weight of the composition.

Apart from the abovementioned substances, the compositions can, if appropriate, comprise the additives customary in cosmetics, for example perfume, dyes, refatting agents, complexing and sequestering agents, pearlizing agents, plant extracts, vitamins, active ingredients, pigments which have a coloring effect, softening, moisturizing and/or humectant substances, or other customary constituents of a cosmetic or dermatological formulation, such as alcohols, polyols, polymers, organic acids for pH adjustment, foam stabilizers, electrolytes, organic solvents or silicone derivatives.

With regard to the specified further ingredients known to the person skilled in the art for the compositions, reference may be made to "Kosmetik und Hygiene von Kopf bis Fuβ" [Cosmetics and hygiene from head to toe], Ed. W. Umbach, 3rd Edition, Wiley-VCH, 2004, pp. 123-128, to which reference is made at this point in its entirety.

Ethoxylated Glycerol Fatty Acid Esters

The compositions according to the invention such as shampoos and haircare compositions comprise, if appropriate, ethoxylated oils selected from the group of ethoxylated glycerol fatty acid esters, particularly preferably PEG-10 olive oil glycerides, PEG-11 avocado oil glycerides, PEG-11 cocoa butter glycerides, PEG-13 sunflower oil glycerides, PEG-15 glyceryl isostearate, PEG-9 coconut fatty acid glycerides, PEG-54 hydrogenated castor oil, PEG-7 hydrogenated castor oil, PEG-60 hydrogenated castor oil, jojoba oil ethoxylate (PEG-26 jojoba fatty acids, PEG-26 jojoba alcohol), glycereth-5 cocoate, PEG-9 coconut fatty acid glycerides, PEG-7 glyceryl cocoate, PEG-45 palm kernel oil glycerides, PEG-35 castor oil, olive oil PEG-7 ester, PEG-6 caprylic acid/capric acid glycerides, PEG-10 olive oil glycerides, PEG-13 sunflower oil glycerides, PEG-7 hydrogenated castor oil, hydrogenated palm kernel oil glyceride PEG-6 ester, PEG-20 corn oil glycerides, PEG-18 glyceryl oleate cocoate, PEG-40 hydrogenated castor oil, PEG-40 castor oil, PEG-60 hydrogenated castor oil, PEG-60 corn oil glycerides, PEG-54 hydrogenated castor oil, PEG-45 palm kernel oil glycerides, PEG-80 glyceryl cocoate, PEG-60 almond oil glycerides, PEG-60 evening primrose glycerides, PEG-200 hydrogenated glyceryl palmate, PEG-90 glyceryl isostearate.

Preferred ethoxylated oils are PEG-7 glyceryl cocoate, PEG-9 coconut glyceride, PEG-40 hydrogenated castor oil, PEG-200 hydrogenated glyceryl palmate.

Ethoxylated glycerol fatty acid esters are used in aqueous cleaning formulations for various purposes. Glycerol fatty acid esters with a degree of ethoxylation of about 30-50 serve as solubility promoters for nonpolar substances such as perfume oils. Highly ethoxylated glycerol fatty acid esters are used as thickeners.

Active Ingredients

It has been found that active ingredients of varying solubility can be homogeneously incorporated into the compositions according to the invention, such as shampoos and haircare compositions. The substantivity of the active ingredients on the hair is higher from the described composition than from conventional surfactant-containing cleaning formulations.

According to the invention, the active ingredients (one or more compounds) can advantageously be selected from the group consisting of acetylsalicylic acid, atropine, azulene, hydrocortisone and derivatives thereof, e.g. hydrocortisone 17-valerate, vitamins of the B and D series, in particular vitamin B1, vitamin B12, vitamin D, vitamin A and derivatives thereof, such as retinyl palmitate, vitamin E or derivatives thereof, such as, for example, tocopheryl acetate, vitamin C and derivatives thereof, such as, for example, ascorbyl glucoside, but also niacinamide, panthenol, bisabolol, polydocanol, unsaturated fatty acids, such as, for example, the essential fatty acids (usually referred to as vitamin F), in particular γ-linolenic acid, oleic acid, eicosapentaenoic acid, docosahexaenoic acid and derivatives thereof, chloroamphenicol, caffeine, prostaglandins, thymol, camphor, squalene, extracts or other products of vegetable and animal origin, e.g. evening primrose oil, borage oil or currant seed oil, fish oils, cod-liver oil, but also ceramides and ceramide-like compounds, incense extract, green tea extract, water lily extract, liquorice extract, hamamelis, antidandruff active ingredients (e.g. selenium disulfide, zinc pyrithion, piroctone, olamine, climbazole, octopirox, polydocanol and combinations thereof), complex active ingredients, such as, for example, those from γ-oryzanol and calcium salts, such as calcium panthotenate, calcium chloride, calcium acetate.

It is also advantageous to select the active ingredients from the group of refatting substances, for example purcellin oil, Eucerit® and Neocerit®.

The active ingredient or active ingredients is/are also particularly advantageously selected from the group of NO synthase inhibitors, particularly if the compositions according to the invention are to serve for the treatment and prophylaxis of the symptoms of intrinsic and/or extrinsic aging and also for the treatment and prophylaxis of the harmful effects of ultraviolet radiation on the hair. A preferred NO synthase inhibitor is nitroarginine.

Furthermore, the active ingredient or active ingredients is/are advantageously selected from the group consisting of catechins and bile acid esters of catechins and aqueous or organic extracts from plants or parts of plants which have a content of catechins or bile acid esters of catechins, such as, for example, the leaves of the plant family Theaceae, in particular of the species *Camellia sinensis* (green tea). Their typical ingredients (e.g. polyphenols or catechins, caffeine, vitamins, sugars, minerals, amino acids, lipids) are particularly advantageous.

Catechins are a group of compounds which are to be regarded as hydrogenated flavones or anthocyanidins and are derivatives of "catechins" (catechol, 3,3',4',5,7-flavanpentaol, 2-(3,4-dihydroxyphenyl)chroman-3,5,7-triol). Epicatechin ((2R,3R)-3,3',4',5,7-flavanpentaol) is also an advantageous active ingredient within the context of the present invention.

Also advantageous are plant extracts with a content of catechins, in particular extracts of green tea, such as, for example, extracts from leaves of the plants of the *Camellia* spec. species, very particularly of the tea varieties *Camellia sinenis, C. assamica, C. taliensis* and *C. inawadiensis* and hybrids of these with, for example, *Camellia japonica*.

Preferred active ingredients are also polyphenols and catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin, (−)-epigallocatechin gallate.

Flavone and its derivatives (often also collectively called "flavones") are also advantageous active ingredients within the context of the present invention. They are characterized by the following basic structure (substitution positions given):

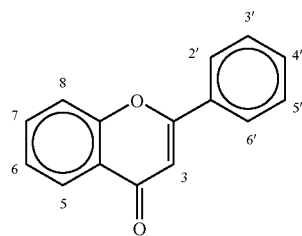

Some of the more important flavones which can also preferably be used in compositions according to the invention are listed in Table 2 below.

TABLE 2

| Flavones | | | | | | | | |
|---|---|---|---|---|---|---|---|---|
| | OH substitution positions | | | | | | | |
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | − | − | − | − | − | − | − |
| Galangin | + | − | − | − | − | − | − | − |
| Abigenin | − | − | + | − | − | − | − | − |
| Fisetin | + | − | + | − | − | + | + | − |
| Luteolin | − | − | + | − | − | + | + | − |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones generally occur in glycosidylated form.

According to the invention, the flavonoids are preferably selected from the group of substances of the general formula

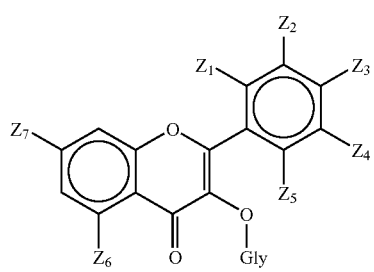

where $Z_1$ to $Z_7$, independently of one another, are selected from the group H, OH, alkoxy and hydroxyalkoxy, where the alkoxy and/or hydroxyalkoxy groups may be branched or unbranched and may have 1 to 18 carbon atoms, and where Gly is selected from the group of mono- and oligoglycoside radicals.

According to the invention, the flavonoids can, however, also be selected advantageously from the group of substances of the general formula

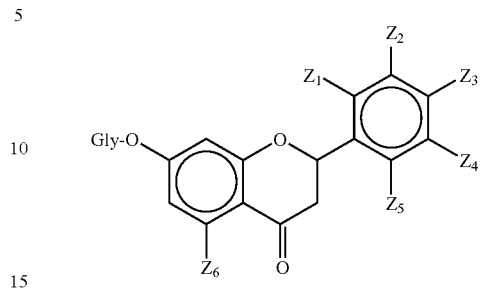

where $Z_1$ to $Z_6$, independently of one another, are selected from the group H, OH, alkoxy and hydroxyalkoxy, where the alkoxy and/or hydroxyalkoxy groups may be branched or unbranched and may have 1 to 18 carbon atoms, and where Gly is selected from the group of mono- and oligoglycoside radicals.

Preferably, such structures can be selected from the group of substances of the general formula

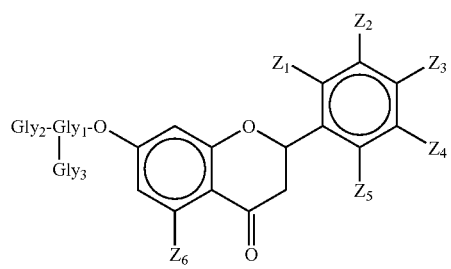

where $Z_1$ to $Z_6$, independently of one another, are as specified above, and $Gly_1$, $Gly_2$ and $Gly_3$, independently of one another, are monoglycoside radicals or oligoglycoside radicals. $Gly_2$ and $Gly_3$ can also individually or together be saturations by hydrogen atoms.

Preferably, $Gly_1$, $Gly_2$ and $Gly_3$, independently of one another, are selected from the group of hexosyl radicals, in particular rhamnosyl radicals and glucosyl radicals. However, other hexosyl radicals, for example aliosyl, altrosyl, galactosyl, gulosyl, idosyl, mannosyl and talosyl are also to be used advantageously if appropriate. It may also be advantageous according to the invention to use pentosyl radicals.

Advantageously, $Z_1$ to $Z_5$, independently of one another, are selected from the group H, OH, methoxy, ethoxy and 2-hydroxyethoxy, and the flavone glycosides correspond to the general structural formula

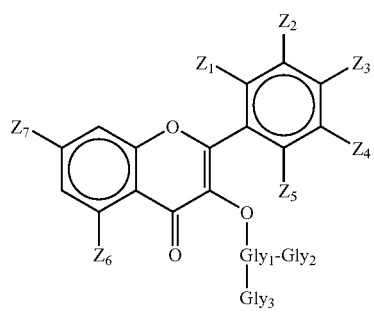

The flavone glycosides are particularly advantageously selected from the group which is given by the following structure

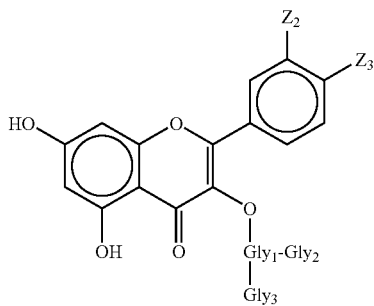

where $Gly_1$, $Gly_2$ and $Gly_3$, independently of one another, are monoglycoside radicals or oligoglycoside radicals. $Gly_2$ and $Gly_3$ can also individually or together be saturations by hydrogen atoms.

Preferably, $Gly_1$, $Gly_2$ and $Gly_3$, independently of one another, are selected from the group of hexosyl radicals, in particular rhamnosyl radicals and glucosyl radicals. However, other hexosyl radicals, for example allosyl, altrosyl, galactosyl, gulosyl, idosyl, mannosyl and talosyl, are also to be used advantageously, if appropriate. It may also be advantageous according to the invention to use pentosyl radicals.

Within the context of the present invention, it is particularly advantageous to select the flavone glycoside or flavone glycosides from the group α-glucosylrutin, α-glucosylmyricetin, α-glucosylisoquercitrin, α-glucosylisoquercetin and α-glucosylquercitrin.

Further advantageous active ingredients are sericoside, pyridoxol, vitamin K, biotin and aroma substances.

Furthermore, the active ingredients (one or more compounds) can also very advantageously be selected from the group of hydrophilic active ingredients, in particular from the following group:

α-hydroxy acids, such as lactic acid or salicylic acid and salts thereof, such as, for example, Na-lactate, Ca-lactate, TEA-lactate, urea, allantoin, serine, sorbitol, glycerol, milk proteins, panthenol, chitosan.

The list of specified active ingredients and active ingredient combinations which can be used in the compositions according to the invention is not of course intended to be limiting. The active ingredients can be used individually or in any combinations with one another.

The amount of such active ingredients (one or more compounds) in the compositions according to the invention is preferably 0.001 to 30% by weight, particularly preferably 0.05 to 20% by weight, in particular 1 to 10% by weight, based on the total weight of the composition.

The specified and further active ingredients which can be used in the compositions according to the invention are given in DE 103 18 526 A1 on pages 12 to 17, to which reference is made at this point in its entirety.

Pearlescent Waxes

Suitable pearlescent waxes are, for example: alkylene glycol esters, specifically ethylene glycol distearate; fatty acid alkanolamides, specifically coconut fatty acid diethanoamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates which have a total of at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

The compositions according to the invention can further comprise glitter substances and/or other effect substances (e.g. color streaks).

Emulsifiers

In one preferred embodiment, the shampoos and haircare compositions according to the invention additionally comprise emulsifiers. Suitable emulsifiers are, for example, non-ionogenic surfactants from at least one of the following groups:

(1) addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

(2) C12/18 fatty acid mono- and diesters of addition products of from 1 to 30 mol of ethylene oxide onto glycerol;

(3) glycerol mono- and diesters and sorbitan mono- and diesters of saturated and unsaturated fatty acids having 6 to 22 carbon atoms and ethylene oxide addition products thereof;

(4) alkyl mono- and oligoglycosides having 8 to 22 carbon atoms in the alkyl radical and ethoxylated analogs thereof;

(5) addition products of from 15 to 60 mol of ethylene oxide onto oils, for example onto castor oil and/or hydrogenated castor oil;

(6) polyol, and in particular polyglycerol, esters, such as, for example, polyglycerol polyricinoleate, polyglycerol poly-12-hydroxystearate or polyglycerol dimerate. Mixtures of compounds from two or more of these classes of substances are likewise suitable;

(7) addition products of from 2 to 15 mol of ethylene oxide onto castor oil and/or hydrogenated castor oil;

(8) partial esters based on linear, branched, unsaturated or saturated $C_{5/22}$-fatty acids, ricinolic acid, and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside), and polyglucosides (e.g. cellulose);

(9) mono-, di- and trialkyl phosphates, and mono-, di- and/or tri-PEG alkyl phosphates and salts thereof;

(10) wool wax alcohols;

(11) polysiloxane-polyalkyl-polyether copolymers and corresponding derivatives;

(12) mixed esters of pentaerythritol, fatty acids, citric acid, and fatty alcohol according to DE-PS 1165574 and/or mixed esters of fatty acids having 6 to 22 carbon atoms, methylglucose and polyols, preferably glycerol or polyglycerol, and

(13) polyalkylene glycols.

The addition products of ethylene oxide and/or of propylene oxide onto fatty alcohols, fatty acids, alkylphenols, glycerol mono- and diesters, and sorbitan mono- and diesters of fatty acids or onto castor oil are known, commercially available products. These are homolog mixtures whose average degree of alkoxylation corresponds to the ratio of the quantitative amounts of ethylene oxide and/or propylene oxide and substrate with which the addition reaction is carried out. $C_{12}$ to $C_{18}$-fatty acid mono- and diesters of addition products of ethylene oxide onto glycerol are known from DE-C 2024051 as refatting agents for cosmetic preparations. $C_8$ to $C_{18}$-alkyl mono- and oligoglycosides, their preparation and their use are known from the prior art. Their preparation takes place in particular by reacting glucose or oligosaccharides with primary alcohols having 8 to 18 carbon atoms. As regards the glycoside ester, either monoglycosides in which a cyclic sugar radical is bonded glycosidically to the fatty alcohol, or oligomeric glycosides with a degree of oligomerization up to preferably about 8 are suitable. The degree of oligomerization here is a statistical average value which is based on a homolog distribution customary for such technical products.

Furthermore, zwitterionic surfactants can be used as emulsifiers. Zwitterionic surfactants is the term used to refer to those surface-active compounds which carry at least one quaternary ammonium group and at least one carboxylate and/or one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocacylaminoethyl hydroxyethylcarboxy-methyl glycinate.

Of particular preference is the fatty acid amide derivative known under the CTFA name Cocamidopropyl Betaine. Likewise suitable emulsifiers are ampholytic surfactants. Ampholytic surfactants are understood as meaning those surface-active compounds which, apart from a $C_8$ to $C_{18}$-alkyl or -acyl group, comprise at least one free amino group and at least one —COOH and/or —SO3H group in the molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12}$ to $C_{18}$-acylsarcosine.

Besides the ampholytic emulsifiers, quaternary emulsifiers are also suitable, particular preference being given to those of the ester quat type, preferably methyl-quaternized difatty acid triethanolamine ester salts.

Perfume Oils

If appropriate, the compositions according to the invention, such as shampoos and haircare compositions, can comprise perfume oils. Perfume oils which may be mentioned are, for example, mixtures of natural and synthetic fragrances. Natural fragrances are extracts from flowers (lily, lavender, rose, jasmine, neroli, Ylang-Ylang), stems and leaves (geranium, patchouli, petit grain), fruits (anis, coriander, caraway, juniper), fruit peels (bergamot, lemon, orange), roots (mace, angelica, celery, cardamom, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoe, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, 4-tert-butyl cyclohexyl acetate, linalyl acetate, dimethylbenzylcarbinyl acetate, phenylethyl acetate, linalyl benzoate, benzyl formate, ethylmethyl phenylglycinate, allyl cyclohexylpropionate, styrallyl propionate and benzyl salicylate.

The ethers include, for example, benzyl ethyl ether, the aldehydes include, for example, the linear alkanals having 8 to 18 carbon atoms, citral, citronellal, citronellyloxyacetaldehyde, cyclamenaldehyde, hydroxycitronellal, lilial and bourgeonat, the ketones include, for example, the ionones, ∝-isomethylions and methyl cedryl ketone, the alcohols include anethol, citronellol, eugenol, isoeugenol, geraniol, linalool, phenylethyl alcohol and terioneol, and the hydrocarbons include primarily the terpenes and balsams. However, preference is given to using mixtures of different fragrances which together produce a pleasing scent note. Essential oils of lower volatility, which are mostly used as aroma components, are also suitable as perfume oils, e.g. sage oil, chamomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzyl acetone, cyclamenaldehyde, linalool, Boisambrene®Forte, ambroxan, indol, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix®Coeur, iso-E-Super®, Fixolide®NP, evernyl, iraldein gamma, phenylacetic acid, geranyl acetate, benzyl acetate, rose oxide, romillat, irotyl and floramat alone or in mixtures.

Pigments

If appropriate, the compositions according to the invention such as shampoos and haircare compositions also comprise pigments.

The pigments are present in the product mass in undissolved form and may be present in an amount of from 0.01 to 25% by weight, particularly preferably from 5 to 15% by weight. The preferred particle size is 1 to 200 μm, in particular 3 to 150 μm, and particularly preferably 10 to 100 μm. The pigments are colorants which are virtually insoluble in the application medium and may be inorganic or organic. Inorganic-organic mixed pigments are also possible. Preference is given to inorganic pigments. The advantage of the inorganic pigments is their excellent fastness to light, weather and temperature. The inorganic pigments may be of natural origin, for example prepared from chalk, ocker, umbra, green earth, burnt sienna or graphite. The pigments may be white pigments, such as, for example, titanium dioxide or zinc oxide, black pigments, such as, for example, iron oxide black, colored pigments, such as, for example ultramarine or iron oxide red, luster pigments, metal effect pigments, pearlescent pigments, and fluorescent and phosphorescent pigments, where preferably at least one pigment is a colored, nonwhite pigment.

Metal oxides, hydroxides and oxide hydrates, mixed phase pigments sulfur-containing silicates, metal sulfides, complex metal cyanides, metal sulfates, chromates and molybdates, and also the metals themselves (bronze pigments) are suitable. Of particular suitability are titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, pigment blue 29), chromium oxide hydrate (C177289), iron blue (ferric ferrocyanide, C17751 0), carmine (cochineal).

Particular preference is given to pearlescent and colored pigments based on mica which are coated with a metal oxide or a metal oxychloride such as titanium dioxide or bismuth oxychloride, and, if appropriate, further color-imparting substances, such as iron oxides, iron blue, ultramarine, carmine etc., and where the color can be determined by varying the layer thickness. Pigments of this type are sold, for example, under the trade names Rona®, Colorona®, Dichrona® and Timiron® (Merck).

Organic pigments are, for example, the natural pigments sepia, gamboge, charcoal, Cassel brown, indigo, chlorophyll and other plant pigments. Synthetic organic pigments are, for example, azo pigments, anthraquinoids, indigoids, dioxazine, quinacridone, phthalocyanine, isoindolinone, perylene and perinone, metal complex, alkali blue and diketopyrrolopyrrole pigments.

In one embodiment, the composition according to the invention comprises 0.01 to 10% by weight, particularly preferably from 0.05 to 5% by weight, of at least one particulate substance. Suitable substances are, for example, substances which are solid at room temperature (25° C.) and are present in the form of particles. For example, silica, silicates, aluminates, clay earths, mica, salts, in particular inorganic metal salts, metal oxides, e.g. titanium dioxide, minerals and polymer particles are suitable.

The particles are present in the composition in undissolved form, preferably in stably dispersed form and, following application to the application surface and evaporation of the solvent, can settle out in solid form.

Preferred particulate substances are silica (silica gel, silicon dioxide) and metal salts, in particular inorganic metal salts, particular preference being given to silica. Metal salts are, for example, alkali metal or alkaline earth metal halides, such as sodium chloride or potassium chloride; alkali metal or alkaline earth metal sulfates, such as sodium sulfate or magnesium sulfate.

Polymers

The compositions according to the invention may also comprise additional polymers. Suitable polymers are, for example, further cationic polymers with the INCI name Polyquaternium, e.g. copolymers of vinylpyrrolidone/N-vinylimidazolium salts (Luviquat® FC, Luviquat® HM, Luviquat® MS, Luviquat® Care, Luviquat® UltraCare), copolymers of N-vinylpyrrolidone/dimethylaminoethyl methacrylate, quaternized with diethyl sulfate (Luviquat® PQ 11), copolymers of N-vinylcaprolactam/N-vinyl-pyrrolidone/N-vinylimidazolium salts (Luviquat® Hold); cationic cellulose derivatives (Polyquaternium-4, -10, -67), acrylamido copolymers (Polyquaternium-7) and chitosan. Suitable cationic (quaternized) polymers are also Merquat® (polymer based on dimethyldiallylammonium chloride), Gafquat® (quaternary polymers which are formed by reacting polyvinylpyrrolidone with quaternary ammonium compounds), polymer JR (hydroxyethylcellulose with cationic groups) and cationic polymers based on plants, e.g. guar polymers, such as the Jaguar® grades from Rhodia.

Further suitable polymers are also neutral polymers, such as polyvinylpyrrolidones, copolymers of N-vinylpyrrolidone and vinyl acetate and/or vinylpropionate and/or stearyl (meth)acrylate, polysiloxanes, polyvinylcaprolactam and other copolymers with N-vinylpyrrolidone, copolymers with N-vinylformamide, and (partial) hydrolyzates thereof, polyethyleneimines and salts thereof, polyvinylamines and salts thereof, cellulose derivatives, polysaccharide derivatives, polyaspartic acid salts and derivatives. These include, for example, Luviflex® Swing (partially saponified copolymer of polyvinyl acetate and polyethylene glycol, BASF) or Kollicoat® IR. Suitable polymers are also the (meth)acrylamide copolymers described in WO 03/092640, in particular those described as Examples 1 to 50 (Table 1, page 40 et seq.) and Examples 51 to 65 (Table 2, page 43), to which reference is hereby made in its entirety.

Suitable polymers are also nonionic, water-soluble or water-dispersible polymers or oligomers, such as polyvinylcaprolactam, e.g. Luviskol® Plus (BASF), or polyvinylpyrrolidone and copolymers thereof, in particular with vinyl esters, such as vinyl acetate, e.g. Luviskol® VA 64 (BASF); polyamides, e.g. based on itaconic acid and aliphatic diamines, as described, for example, in DE-A-43 33 238.

Suitable polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and also zwitterionic polymers as are disclosed, for example, in the German patent applications DE 39 29 973, DE 21 50 557, DE 28 17 369 and DE 37 08 451. Acrylamidopropyltrimethylammonium chloride/acrylic acid or methacrylic acid copolymers and alkali metal and ammonium salts thereof are preferred zwitterionic polymers.

Furthermore, suitable zwitterionic polymers are methacroylethylbetain/methacrylate copolymers, which are commercially available under the name Amersette® (AMERCHOL), and copolymers of hydroxyethyl methacrylate, methyl methacrylate, N,N-dimethylaminoethyl methacrylate and acrylic acid (Jordapon®).

Suitable polymers are also nonionic, siloxane-containing, water-soluble or -dispersible polymers, e.g. polyethersiloxanes, such as Tegopren® (Goldschmidt) or Belsil® (Wacker).

Furthermore, biopolymers are also suitable, i.e. polymers which are obtained from naturally renewable raw materials and are composed of natural monomer building blocks, e.g. cellulose derivatives, chitin, chitosan, DNA, hyaluronic acid and RNA derivatives.

Further preparations according to the invention comprise at least one further water-soluble polymer, in particular chitosans (poly(D-glucosamines)) of varying molecular weight and/or chitosan derivatives.

Anionic Polymers

Further polymers suitable for the preparations according to the invention are copolymers containing carboxylic acid groups. These are polyelectrolytes with a relatively large number of anionically dissociable groups in the main chain and/or one side chain. They are capable of forming polyelectrolyte complexes (simplexes) with the cationic polymers.

In one embodiment, the polyelectrolyte complexes used in the compositions according to the invention have an excess of anionogenic/anionic groups.

Besides at least one of the cationic polymers suitable for the use according to the invention, the polyelectrolyte complexes also comprise at least one polymer containing acid groups.

The polyelectrolyte complexes comprise, for example, cationic polymers and polymers containing acid groups in a quantitative weight ratio of from about 50:1 to 1:20, particularly preferably from 20:1 to 1:5.

Suitable polymers containing carboxylic acid groups are obtainable, for example, by free-radical polymerization of $\alpha,\beta$-ethylenically unsaturated monomers. The process uses monomers m1) which comprise at least one free-radically polymerizable, $\alpha,\beta$-ethylenically unsaturated double bond and at least one anionogenic and/or anionic group per molecule.

Suitable polymers containing carboxylic acid groups are also polyurethanes containing carboxylic acid groups. Preferably, the monomers are selected from monoethylenically unsaturated carboxylic acids, sulfonic acids, phosphonic acids and mixtures thereof. The monomers m1) include monoethylenically unsaturated mono- and dicarboxylic acids having 3 to 25, preferably 3 to 6, carbon atoms, which can also be used in the form of their salts or anhydrides. Examples thereof are acrylic acid, methacrylic acid, ethacrylic acid, α-chloroacrylic acid, crotonic acid, maleic acid, maleic anhydride, itaconic acid, citraconic acid, mesaconic acid, glutaconic acid, aconitic acid and fumaric acid. The monomers also include the half-esters of monoethylenically unsaturated dicarboxylic acids having 4 to 10, preferably 4 to 6, carbon atoms, e.g. of maleic acid, such as monomethyl maleate. The monomers also include monoethylenically unsaturated sulfonic acids and phosphonic acids, for example vinylsulfonic acid, allylsulfonic acid, sulfoethyl acrylate, sulfoethyl methacrylate, sulfopropyl acrylate, sulfopropyl methacrylate, 2-hydroxy-3-acryloxypropylsulfonic acid, 2-hydroxy-3-methacryloxypropylsulfonic acid, styrenesulfonic acid, 2-acrylamido-2-methylpropanesulfonic acid, vinylphosphonic acid and allylphosphonic acid. The monomers also include the salts of the abovementioned acids, in particular the sodium, potassium and ammonium salts, and also the salts with the abovementioned amines. The monomers can be used as they are or as mixtures with one another. The stated weight fractions all refer to the acid form.

Preferably, the monomer m1) is selected from acrylic acid, methacrylic acid, ethacrylic acid, α-chloroacrylic acid, crotonic acid, maleic acid, maleic anhydride, fumaric acid, itaconic acid, citraconic acid, mesaconic acid, glutaconic acid, aconitic acid and mixtures thereof, particularly preferably acrylic acid, methacrylic acid and mixtures thereof.

The abovementioned monomers m1) can in each case be used individually or in the form of any desired mixtures.

In principle, suitable comonomers for the preparation of the polymers containing carboxylic acid groups are the compounds a) to c) specified previously as components of the cationic polymers with the proviso that the molar fraction of anionogenic and anionic groups which the polymer containing carboxylic acid groups comprises in copolymerized form is greater than the molar fraction of cationogenic and cationic groups.

In one preferred embodiment, the polymers containing carboxylic acid groups comprise at least one copolymerized monomer which is selected from the aforementioned crosslinkers.

Furthermore, the polymers containing carboxylic acid groups preferably comprise at least one copolymerized monomer m2) which is selected from compounds of the general formula VI

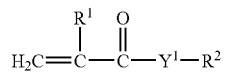

(VI)

in which
$R^1$ is hydrogen or $C_1$-$C_8$-alkyl,
$Y^1$ is O, NH or $NR^3$, and
$R^2$ and $R^3$, independently of one another, are $C_1$-$C_{30}$-alkyl or $C_5$-$C_8$-cycloalkyl, where the alkyl groups may be interrupted by up to four nonadjacent heteroatoms or heteroatom-containing groups which are selected from O, S and NH.

Preferably, $R^1$ in the formula VI is hydrogen or $C_1$-$C_4$-alkyl, in particular hydrogen, methyl or ethyl. Preferably, $R^2$ in the formula VI is $C_1$-$C_8$-alkyl, preferably methyl, ethyl, n-butyl, isobutyl, tert-butyl or a group of the formula —$CH_2$—$CH_2$—NH—$C(CH_3)_3$. If $R^3$ is alkyl, then it is preferably $C_1$-$C_4$-alkyl, such as methyl, ethyl, n-propyl, n-butyl, isobutyl and tert-butyl.

Suitable monomers m2) are, for example, methyl (meth)acrylate, methyl ethacrylate, ethyl (meth)acrylate, ethyl ethacrylate, tert-butyl (meth)acrylate, tert-butyl ethacrylate, n-octyl (meth)acrylate, 1,1,3,3-tetramethylbutyl (meth)acrylate, ethylhexyl (meth)acrylate, n-nonyl (meth)acrylate, n-decyl (meth)acrylate, n-undecyl (meth)acrylate, tridecyl (meth)acrylate, myristyl (meth)acrylate, pentadecyl (meth) acrylate, palmityl (meth)acrylate, heptadecyl (meth)acrylate, nonadecyl (meth)acrylate, arrachinyl (meth)acrylate, behenyl (meth)acrylate, lignocerenyl (meth)acrylate, cerotinyl (meth)acrylate, melissinyl (meth)acrylate, palmitoleinyl (meth)acrylate, oleyl (meth)acrylate, linolyl (meth)acrylate, linolenyl (meth)acrylate, stearyl (meth)acrylate, lauryl (meth)acrylate and mixtures thereof.

Suitable monomers m2) are furthermore acrylamide, methacrylamide, N-methyl(meth)acrylamide, N-ethyl(meth)acrylamide, N-propyl(meth)acrylamide, N-(n-butyl)(meth)acrylamide, N-(tert-butyl)(meth)acrylamide, N,N-dimethyl(meth)acrylamide, N,N-diethyl(meth)acrylamide, piperidinyl(meth)acrylamide and morpholinyl(meth)acrylamide, N-(n-octyl)-(meth)acrylamide, N-(1,1,3,3-tetramethylbutyl)(meth)acrylamide, N-ethyl-hexyl(meth)acrylamide, N-(n-nonyl)(meth)acrylamide, N-(n-decyl)(meth)acrylamide, N-(n-undecyl)(meth)acrylamide, N-tridecyl(meth)acrylamide, N-myristyl-(meth)acrylamide, N-pentadecyl(meth)acrylamide, N-palmityl(meth)acrylamide, N-heptadecyl(meth)acrylamide, N-nonadecyl(meth)acrylamide, N-arrachinyl-(meth)acrylamide, N-behenyl(meth)acrylamide, N-lignocerenyl(meth)acrylamide, N-cerotinyl(meth)acrylamide, N-melissinyl(meth)acrylamide, N-palmitoleinyl-(meth)acrylamide, N-oleyl(meth)acrylamide, N-linolyl(meth)acrylamide, N-linolenyl(meth)acrylamide, N-stearyl(meth)acrylamide and N-lauryl(meth)acrylamide.

Furthermore, the polymers containing carboxylic acids group preferably comprise at least one copolymerized monomer m3) which is selected from compounds of the general formula VII (VII)

$$H_2C=\underset{R^5}{C}-\underset{O}{\overset{\|}{C}}-Y^2-(CH_2CH_2O)_k(CH_2CH(CH_3)O)_l-R^4$$

in which
the order of the alkylene oxide units is arbitrary,
k and l, independently of one another, are an integer from 0 to 1000, where the sum of k and l is at least 5,
$R^4$ is hydrogen, $C_1$-$C_{30}$-alkyl or $C_5$-$C_8$-cycloalkyl,
$R^5$ is hydrogen or $C_1$-$C_8$-alkyl,
$Y^2$ is O or $NR^6$, where $R^6$ is hydrogen, $C_1$-$C_{30}$-alkyl or $C_5$-$C_8$-cycloalkyl.

Preferably, in the formula VII, k is an integer from 1 to 500, in particular 3 to 250.

Preferably, l is an integer from 0 to 100. Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl. Preferably, $R^4$ in the formula VII is hydrogen, methyl, ethyl, n-propyl, isopropyl, n-butyl, sec-butyl, n-pentyl, n-hexyl, octyl, 2-ethylhexyl, decyl, lauryl, palmityl or stearyl. Preferably $Y^2$ in the formula VII is O or NH.

Suitable polyether acrylates VII) are, for example, the polycondensation products of the abovementioned α,β-ethylenically unsaturated mono- and/or dicarboxylic acids and their acid chlorides, amides and anhydrides with polyetherols. Suitable polyetherols can be readily prepared by reacting ethylene oxide, 1,2-propylene oxide and/or epichlorohydrin with a starter molecule, such as water or a short-chain alcohol $R^4$—OH. The alkylene oxides can be used individually, alternately one after the other or as a mixture. The polyether acrylates VII) can be used on their own or in mixtures for preparing the polymers used according to the invention. Suitable polyether acrylates II) are also urethane (meth)acrylates with alkylene oxide groups. Compounds of this type are described in DE 198 38 851 (component e2)), to which reference is made here in its entirety.

Anionic polymers preferred as polymers containing carboxylic acids are, for example, homopolymers and copolymers of acrylic acid and methacrylic acid and salts thereof.

These also include crosslinked polymers of acrylic acid, as are obtainable under the INCI name Carbomer. Such crosslinked homopolymers of acrylic acid are available commercially, for example under the name Carbopol® from Noveon. Preference is also given to hydrophobically modified crosslinked polyacrylate polymers, such as Carbopol® Ultrez 21 from Noveon.

Further examples of suitable anionic polymers are copolymers of acrylic acid and acrylamide and salts thereof; sodium salts of polyhydroxycarboxylic acids, water-soluble or water-dispersible polyesters, polyurethanes and polyureas. Particularly suitable polymers are copolymers of (meth)acrylic acid and polyether acrylates, where the polyether chain is terminated with a $C_8$-$C_{30}$-alkyl radical. These include, for example, acrylate/beheneth-25 methacrylate copolymers, which are available under the name Aculyn® from Rohm and Haas. Particularly suitable polymers are also copolymers of t-butylacrylate, ethyl acrylate, methacrylic acid (e.g. Luvimer® 100P, Luvimer® Pro55), copolymers of ethyl acrylate and methacrylic acid (e.g. Luviumer° MAE), copolymers of N-tert-butylacrylamide, ethyl acrylate, acrylic acid (Ultrahold® 8, Ultrahold® Strong), copolymers of vinyl acetate, crotonic acid and, if appropriate, further vinyl esters (e.g. Luviset® grades), maleic anhydride copolymers, if appropriate reacted with alcohol, anionic polysiloxanes, e.g. carboxy-functional, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkylvinyl esters, $C_4$-$C_{30}$-alkylvinyl ethers and hyaluronic acid. Examples of anionic polymers are also vinyl acetate/crotonic acid copolymers, as are commercially available, for example, under the names Resyn® (National Starch) and Gafset® (GAF) and vinylpyrrolidone/vinyl acrylate copolymers obtainable, for example, under the trade name Luviflex® (BASF). Further suitable polymers are the vinylpyrrolidone/acrylate terpolymer available under the name Luviflex® VBM-35 (BASF) and sodium sulfonate-containing polyamides or sodium sulfonate-containing polyesters.

The group of suitable anionic polymers further comprises, by way of example, Balance® CR (National Starch; acrylate copolymer), Balance® 0/55 (National Starch; acrylate copolymer), Balance® 47 (National Starch; octylacrylamide/acrylates/butylaminoethyl methacrylates copolymer), Aquaflex® FX 64 (ISP; isobutylene/ethylmaleimide/hydroxyethylmaleimide copolymer), Aquaflex® SF-40 (ISP/National Starch; VP/vinyl caprolactam/DMAPA acrylates copolymer), Allianz® LT-120 (ISP/Rohm & Haas; acrylate/C1-2 succinate/hydroxyacrylate copolymer), Aquarez® HS (Eastman; polyester-1), Diaformer® Z-400 (Clariant; methacryloylethylbetaine/methacrylate copolymer), Diaformer® Z-711 (Clariant; methacryloylethyl N-oxide/methacrylate copolymer), Diaformer® Z-712 (Clariant; methacryloylethyl N-oxide/methacrylate copolymer), Omnirez® 2000 (ISP; monoethyl ester of poly(methyl vinyl ether/maleic acid in ethanol), Amphomer® HC (National Starch; acrylate/octylacrylamide copolymer), Amphomer® 28-4910 (National Starch; octylacrylamide/acrylate/butylaminoethyl methacrylate copolymer), Advantage® HC 37 (ISP; terpolymer of vinylcaprolactam/vinylpyrrolidone/dimethylaminoethyl methacrylate), Advantage® LC55 and LC80 or LC A and LC E, Advantage® Plus (ISP; VA/butyl maleate/isobornyl acrylates copolymer), Aculyne® 258 (Rohm & Haas; acrylate/hydroxy ester acrylate copolymer), Luviset® P.U.R. (BASF, polyurethane-1), Luviflex® Silk (BASF), Eastman® AQ 48 (Eastman), Styleze® CC-10 (ISP; VP/DMAPA acrylates copolymer), Styleze® 2000 (ISP; VP/acrylates/lauryl methacrylate copolymer), DynamX® (National Starch; polyurethane-14 AMP-acrylates copolymer), Resyn XP® (National Starch; acrylates/octylacrylamide copolymer), Fixomer® A-30 (Ondeo Nalco; polymethacrylic acid (and) acrylamidomethylpropanesulfonic acid), Fixate® G-100 (Noveon; AMP-acrylates/allyl methacrylate copolymer).

Suitable polymers containing carboxylic acid groups are also the terpolymers of vinylpyrrolidone, $C_1$-$C_{10}$-alkyl, cycloalkyl and aryl (meth)acrylates and acrylic acid described in U.S. Pat. No. 3,405,084. Suitable polymers containing carboxylic acid groups are also the terpolymers of vinylpyrrolidone, tert-butyl (meth)acrylate and (meth)acrylic acid described in EP-A-0 257 444 and EP-A-0 480 280. Suitable polymers containing carboxylic acid groups are also the copolymers described in DE-A-42 23 066 which comprise at least one (meth)acrylic acid ester, (meth)acrylic acid and N-vinylpyrrolidone and/or N-vinylcaprolactam in copolymerized form. Reference is made here to the disclosure of these documents in its entirety.

The abovementioned polymers containing carboxylic acid groups are prepared by known methods, for example solution, precipitation, suspension or emulsion polymerization as described above for the cationic polymers.

Suitable polymers containing carboxylic acid groups are also polyurethanes containing carboxylic acid groups.

EP-A-636361 discloses suitable block copolymers with polysiloxane blocks and polyurethane/polyurea blocks which have carboxylic acid and/or sulfonic acid groups.

Suitable silicone-containing polyurethanes are also described in WO 97/25021 and EP-A-751 162.

Suitable polyurethanes are also described in DE-A-42 25 045, to which reference is hereby made in its entirety.

The acid groups of the polymers containing carboxylic acid groups may be partly or completely neutralized. At least some of the acid groups are then present in deprotonated form, the counterions preferably being selected from alkali metal ions, such as $Na^+$, $K^+$, ammonium ions and organic derivatives thereof etc.

The compositions according to the invention comprising polymer a) and polymer b) are suitable for enhancing or for increasing the deposition amount and deposition rate and also the residence time of further active ingredients likewise present, if appropriate, in these compositions according to the invention, such as, for example, silicones or UV photoprotective filters, on the skin and/or the hair. Substances or compositions which have such effects are also referred to as depositioning aids.

U.S. Pat. No. 6,998,113 describes rinse-off preparations which lead to the skin treated therewith being effectively protected against UV radiation. Some of the preparations described therein comprise cationic polymers. Within the context of the present invention, the mixtures according to the invention of the at least one cationic polymer a) and the at least one water-soluble b) can also be used in the preparations of U.S. Pat. No. 6,998,113. In particular, the mixtures according to the invention can be used for the purpose specified by U.S. Pat. No. 6,998,113 in sunscreen, washing and bathing preparations. Reference is hereby made to the disclosure of U.S. Pat. No. 6,998,113 in its entirety.

Suitable silicones are given, for example, in U.S. Pat. No. 5,935,561, column 13, I. 64 to column 18, I. 61, to which reference is hereby made in its entirety.

By way of representation, mention may be made of:
dimethicones
  polyalkyl- or polyarylsiloxanes (U.S. Pat. No. 5,935,561, column 13, formula I)
  alkylamino-substituted silicones (U.S. Pat. No. 5,935,561, column 14, formula II (amodimethicones))
  cationic silicones (U.S. Pat. No. 5,935,561, columns 14 and 15, formula III)
  trimethylsilylamodimethicones (U.S. Pat. No. 5,935,561, column 15, formula IV)
  silicones according to U.S. Pat. No. 5,935,561, column 15, formula V
cyclic polysiloxanes according to U.S. Pat. No. 5,935,561, column 16, formula VI.

Shampoo Types

Depending on the hair quality or scalp problem, additional requirements are placed, if appropriate, on shampoos. The mode of action of the preferred shampoo types with the most important additional effects or most important specific objectives is described below.

According to the invention, preference is given, for example, to shampoos for normal or rapidly greasing or damaged hair, antidandruff shampoos, baby shampoos and 2-in-1 shampoos (shampoo and rinse in one).

Shampoos for normal hair: hair washing should free hair and scalp from the skin sebum formed in sebaceous glands, the inorganic salts emerging from sweat glands with water, amino acids, urea and lactic acid, flaked-off skin particles, environmental dirt, odors and, if appropriate, residues of hair cosmetic treatments. Normal hair means short to shoulder length hair which is only slightly damaged. Accordingly, the fraction of conditioning auxiliaries should be optimized to this hair type.

Shampoos for rapidly greasing hair increased sebum production of the sebaceous glands in the scalp leads to a straggly, unattractive hairstyle just 1-2 days after hair washing. Oil and wax-like skin sebum constituents weigh down the hair and lower the friction from hair to hair and thus reduce the hairstyle hold. The actual hair cosmetic problem in the case of rapidly greasing hair is thus the premature collapse of voluminous hairstyles. In order to avoid this, it is necessary to prevent the surface of the hair becoming weighed down and too smooth and supple. This is preferably achieved through the surfactant base of washing raw materials that are good at cleaning and of particularly low substantivity. Additional care substances which would be added to the skin sebum, such as refatting substances or conditioning auxiliaries, are only used in shampoos for rapidly greasing hair with the greatest of care, if at all. Voluminizing shampoos for fine hair can be formulated comparably.

Shampoos for dry, stressed (damaged) hair. The structure of the hair in the course of hair growth is changed as a result of mechanical influences such as combing, brushing and especially back combing (combing against the direction of growth), as a result of the effect of UV radiation or visible light and as a result of cosmetic treatments, such as permanent waving, bleaching or coloring. The scale layer of the hair has an increasingly stressed appearance from the root to the end; in extreme cases, it is completely worn away at the end, and the hair ends are split (split ends). Damaged hair can in principle no longer be restored to the condition of healthy hair regrowth. However, it is possible to come very close to this ideal condition with regard to feel, shine and combability through use of shampoos according to the invention with, if appropriate, high fractions of care substances (conditioners).

An even better effect than with a shampoo is achieved with a haircare composition according to the invention for example in the form of a rinse or cure treatment after hair washing.

2-in-1 shampoos according to the invention are particularly strongly caring shampoos in which, through the conception as "shampoo and rinse in one", the additional benefit of care is placed equally alongside the basic benefit of cleaning. 2-in-1 compositions according to the invention comprise increased amounts of conditioners.

Antidandruff shampoos: Compared with antidandruff hair tonics, antidandruff shampoos according to the invention have the advantage that they not only reduce the formation of new visible flakes through corresponding active ingredients to combat an attack of dandruff, and prevent such formation in the case of long-term use, but also remove flakes which have already flaked off with the hair washing. After rinsing out the wash liquor, however, only a small but adequate amount of the active ingredients remains on the scalp and hair. There are various antidandruff active ingredients which can be incorporated into the shampoo compositions according to the invention, such as, for example, zinc pyrithione, ketoconazole, clotrimazole, climbazole or piroctone olamine. In addition, these substances have an effect that normalizes the flaking. The basis of antidandruff shampoos largely corresponds to the formulation of shampoos for normal hair with a good cleaning effect.

Baby shampoos: in a preferred embodiment of the invention, the shampoo preparations according to the invention are baby shampoos. These are optimally skin and mucosa compatible. Combinations of washing raw materials with very good skin compatibility form the basis of these shampoos. Additional substances for further improving the skin and mucosa compatibility and the care properties are advantageously added, such as, for example, nonionic surfactants, protein hydrolyzates and panthenol or bisabolol. All necessary raw materials and auxiliaries, such as preservatives, perfume oils, dyes etc., are selected under the aspect of high compatibility and mildness.

Shampoos for dry scalp: in a further preferred embodiment of the invention, the shampoo preparations according to the invention are shampoos for dry scalp. The primary aim of these shampoos is to prevent the scalp from drying out, since dry scalp can lead to irritation, reddening and inflammation. As in the case of baby shampoos, combinations of washing raw materials with very good skin compatibility form the basis of these shampoos. In addition, if appropriate, refatting agents and humectants, such as, for example, glycerol or urea, can be used.

The shampoo compositions according to the invention can also be present as shampoo concentrates with increased surfactant contents of 20-30%. They are based on special washing raw material combinations and consistency regulators which ensure good distributability and spontaneous foaming ability, even in a small use amount. A particular advantage is, for example, the possibility of achieving the productivity of 200 ml of shampoo with a 100 ml bottle.

Supply Form

It is advantageous if the cosmetic compositions according to the invention are stored in a bottle or squeezable bottle and are applied from this. Accordingly, bottles or squeezable bottles which comprise a composition according to the invention are also in accordance with the invention.

EXAMPLES

The following abbreviations are used below:
dem.: completely demineralized
Q: quaternized, QV1*DMS means: VI was quaternized with DMS
N-vinylpyrrolidone: VP
vinylimidazole: VI
vinylimidazole quaternized with methyl chloride: VI*MeCl
vinylimidazole quaternized with dimethyl sulfate: VI*DMS
dimethylaminoethyl methacrylate: DMAEMA

Example 1

| | | VP/VI*MeCl/DMAEMA 5/75/20 (weight ratio) | | |
|---|---|---|---|---|
| | Amount | Feed material | Content | Fraction (% by wt.) |
| Initial charge | 87.52 g | dem. water | 100.00% | 58.35 |
| | 17.25 g | QVI*MeCl | 60.00% | 6.90 |
| | 1.05 g | VP | 100.00% | 0.70 |
| | 0.06 g | Mercaptoethanol | 100.00% | 0.04 |
| | 4.20 g | DMAEMA | 100.00% | 2.80 |
| Feed 1 | 42.00 g | dem. water | 100.00% | 28.00 |
| | 170.25 g | QVI*MeCl | 60.00% | 68.10 |
| | 6.45 g | VP | 100.00% | 4.30 |
| | 0.39 g | Mercaptoethanol | 100.00% | 0.26 |
| | 25.80 g | DMAEMA | 100.00% | 17.20 |
| Feed 2 | 26.25 g | dem. water | 100.00% | 17.50 |
| | 1.50 g | Wako ® V 50 | 100.00% | 1.00 |
| Addition 3 | 1.90 g | Euxyl ® K 100 | 100.00% | 1.27 (0.5%) |

The initial charge was weighed in, flushed with nitrogen atmosphere and covered and heated to 57° C. 6.8% by weight of feed 2 were added. Following initial polymerization for 15 minutes, feed 1 and 62.7% by weight of feed 2 were added over the course of 5 hours. The remainder of feed 2 was then added immediately over the course of 45 minutes. The solution was heated to 70° C. and the polymerization was continued for a further hour. The mixture was then cooled to below 40° C. and addition 3 was added.

Example 2

| | | VP/QVI*DMS/DMAEMA 5/75/20 (weight ratio) | | |
|---|---|---|---|---|
| | Amount | Feed material | Content | Fraction |
| Initial charge | 72.72 g | dem. water | 100.00% | 40.40 |
| | 27.60 g | QVI*DMS | 45.00% | 6.90 |
| | 1.26 g | VP | 100.00% | 0.70 |
| | 0.72 g | Mercaptoethanol | 10.00% | 0.04 |
| | 5.04 g | DMAEMA | 100.00% | 2.80 |

-continued

| | | VP/QVI*DMS/DMAEMA 5/75/20 (weight ratio) | | |
|---|---|---|---|---|
| | Amount | Feed material | Content | Fraction |
| Feed 1 | 2.85 g | dem. water | 100.00% | 1.58 |
| | 272.40 g | QVI*DMS | 45.00% | 68.10 |
| | 7.74 g | VP | 100.00% | 4.30 |
| | 4.68 g | Mercaptoethanol | 10.00% | 0.26 |
| | 30.96 g | DMAEMA | 100.00% | 17.20 |
| Feed 2 | 31.50 g | dem. water | 100.00% | 17.50 |
| | 1.80 g | Wako ® V 50 | 100.00% | 1.00 |
| Addition 3 | 2.28 g | Euxyl ® K 100 | 100.00% | 1.27 (0.5%) |

The initial charge (pH=9.7) was weighed in, flushed with nitrogen atmosphere and covered and heated to 57° C. 6.8% by weight of feed 2 were added. After initial polymerization for 15 minutes, feed 1 and 62.7% by weight of feed 2 were added over the course of 5 hours. The remainder of feed 2 was then added immediately over the course of 45 minutes. The solution was heated to 70° C. and the polymerization was continued for a further hour. The mixture was then cooled to below 40° C. and addition 3 was added.

Example 3

| | | VP/QVI*DMS/DMAEMA 3.6/82/14.4 (weight ratio) | | |
|---|---|---|---|---|
| | Amount | Feed material | Content | Fraction |
| Initial charge | 61.68 g | dem. water | 100.00% | 34.27 |
| | 30.16 g | QVI*DMS | 45.00% | 7.54 |
| | 0.90 g | VP | 100.00% | 0.50 |
| | 0.72 g | Mercaptoethanol | 10.00% | 0.04 |
| | 3.64 g | DMAEMA | 100.00% | 2.02 |
| Feed 1 | 297.84 g | QVI*DMS | 45.00% | 74.46 |
| | 5.58 g | VP | 100.00% | 3.10 |
| | 4.68 g | Mercaptoethanol | 10.00% | 0.26 |
| | 22.28 g | DMAEMA | 100.00% | 12.38 |
| Feed 2 | 30.00 g | dem. water | 100.00% | 16.67 |
| | 1.80 g | Wako ® V 50 | 100.00% | 1.00 |
| Addition 3 | 2.29 g | Euxyl ® K 100 | 100.00% | 1.27 (0.5%) |

The initial charge (pH=9.5) was weighed in, flushed with nitrogen atmosphere and covered and heated to 57° C. 6.8% by weight of feed 2 were added. After initial polymerization for 15 minutes, feed 1 and 62.7% by weight of feed 2 were added over the course of 5 hours. The remainder of feed 2 was then immediately added over the course of 45 minutes. The solution was heated to 70° C. and the polymerization was continued for a further hour. The mixture was then cooled to below 40° C. and addition 3 was added.

Comparative Examples

| | | V1:VP/QVI*DMS 25/75 (weight ratio) | | |
|---|---|---|---|---|
| | Amount | Feed material | Content | Fraction |
| Initial charge | 72.72 g | dem. water | 100.00% | 40.40 |
| | 27.60 g | QVI*DMS | 45.00% | 6.90 |
| | 6.3 g | VP | 100.00% | 3.50 |
| | 0.72 g | Mercaptoethanol | 10.00% | 0.04 |

-continued

V1:VP/QVI*DMS 25/75 (weight ratio)

|  | Amount | Feed material | Content | Fraction |
|---|---|---|---|---|
| Feed 1 | 272.4 g | QVI*DMS | 45.00% | 68.10 |
|  | 38.7 g | VP | 100.00% | 21.50 |
|  | 4.68 g | Mercaptoethanol | 10.00% | 0.26 |
|  | 0.39 g | NaOH | 25.00% | 0.06 |
| Feed 2 | 31.50 g | dem. water | 100.00% | 17.5 |
|  | 1.80 g | Wako ® V 50 | 100.00% | 1.00 |
| Addition 3 | 2.28 g | Euxyl ® K 100 | 100.00% | 1.27 (0.5%) |

Comparative Example 2

VP/QVI*MeCl 25/75 (weight ratio)

|  | Amount | Feed material | Content | Fraction |
|---|---|---|---|---|
| Initial charge | 87.52 g | dem. water | 100.00% | 58.35 |
|  | 17.25 g | QVI*MeCl | 60.00% | 6.90 |
|  | 5.20 g | VP | 100.00% | 3.50 |
|  | 0.06 g | Mercaptoethanol | 10.00% | 0.04 |
| Feed 1 | 42.0 g | dem. water | 100.00% | 28 |
|  | 170.25 g | QVI*MeCl | 60.00% | 68.10 |
|  | 32.30 g | VP | 100.00% | 21.50 |
|  | 0.39 g | Mercaptoethanol | 10.00% | 0.26 |
|  | 0.42 g | NaOH | 10.00% | 0.033 |
| Feed 2 | 26.25 g | dem. water | 100.00% | 17.50 |
|  | 1.50 g | Wako ® V 50 | 100.00% | 1.00 |
| Addition 3 | 1.90 g | Euxyl ® K 100 | 100.00% | 1.27 (0.5%) |

Determination of the K Values

The K values were measured in accordance with Fikentscher, Cellulosechemie, Vol. 13, pp. 58 to 64 (1932) at 25° C. in aqueous 3% strength by weight NaCl solution and are a measure of the molecular weight. The solution of the polymers comprises 1 g of polymer in 100 ml of solution.

The K value is measured in a micro-Ubbelohde capillary type M Ic from Schott.

| Polymer from example | K value |
|---|---|
| 1 | 49.0 |
| 2 | 47.2 |
| 3 | 44.9 |
| Comparative example 1 | 29.3 |
| Comparative example 2 | 35.0 |

Wet Combability (European, Bleached Hair Tresses):
Determination of Blank Value

Before the determination, the bleached hair tress (length about 24 cm/weight 2.7-3.3 g) was firstly shampooed twice with Texapon®NSO for a total of 1 minute and rinsed for 1 minute in order to achieve a defined wetness and swelling.

Then, the tress was precombed such that knots were no longer present in the hair.

The tress was then fixed to the holder and combed into the fine-toothed side of the test comb using the fine-toothed side of the comb. The hair was placed in the test comb for each measurement evenly and free from tension.

The measurement was started and evaluated using the EGRANUDO® software (Frank). The measurement was repeated 5-10 times. The measurements were carried out in a climatically controlled room at about 65% relative humidity and 21° C.

The calculated average was noted together with the standard deviation.

Storage Stability of the Shampoo:

The shampoos (0.5% active ingredient) were stored for 3 months at 40° C. In each case after 2 and 6 weeks and after 3 months, the shampoos were assessed and investigated for possible precipitations.

The assessment is graded in:

sediment, precipitate, slight precipitate and coating.

Shampoo Formulation:

| 35.70 g | Texapon ® NSO |
|---|---|
| 12.50 g | Tego Betain L 7 |
| 1 g | Polymer solution |
|  | (20% strength by weight solution of the solid polymer) |
| 0.10 g | Euxyl ® K 100 |
| ad 100 g | Water |
| 1.00 g | NaCl |

5 g of the shampoo to be tested were applied, shampooed for 1 min, rinsed for 1 min, squeezed on filter paper and combed, and the measurement was determined.

Evaluation:

Combing force decrease wet=100−(measurement*100/blank value); data in %

Instruments used: Stress/strain tester from Frank

Digital balance (top-pan balance)

| Polymer from example | Decrease in combing force [%] | Stability of the shampoo after 3 monhts |
|---|---|---|
| 1 | 66 | stable |
| 2 | 54 | stable |
| 3 | 59 | stable |
| C1 | 25 | stable |
| C2 | 37 | stable |

The stability of the shampoo is assessed as follows:

stable: after storage for three months at RT and at 40° C., the shampoos remain stable.

Examples of Cosmetic Compositions:

Hair Cosmetic Composition (General)

a) 0.01 to 5% by weight of a polymer suitable according to the invention b) 25 to 99.99% by weight of water and/or alcohol c) 0 to 95.99% by weight of further constituents Alcohol is understood as meaning all alcohols customary in cosmetics, e.g. ethanol, isopropanol, n-propanol.

Further constituents are to be understood as meaning the additives customary in cosmetics, for example propellants, antifoams, interface-active compounds, i.e. surfactants, emulsifiers, foam formers and solubilizers. The interface-active compounds used may be anionic, cationic, amphoteric or neutral. Further customary constituents may also be, for example, preservatives, perfume oils, opacifiers, active ingredients, UV filters, care substances, such as panthenol, collagen, vitamins, protein hydrolyzates, alpha- and beta-hydroxycarboxylic acids, chitosan, protein hydrolyzates, cosmetic polymers, stabilizers, pH regulators, dyes, viscosity regulators, gel formers, dyes, salts, humectants, refatting agents, complexing agents and further customary additives.

Shampoo Formulation/Shower Gel Formulation

Preferred shampoo formulations or shower gel formulations comprise a) 0.01 to 5% by weight of a polymer suitable according to the invention
b) 25 to 99.99% by weight of water
c) 0-5% by weight of a further conditioning agent
d) 0-30% by weight of further cosmetic constituents Furthermore, all anionic, neutral, amphoteric or cationic surfactants used customarily in shampoos can be used in the shampoo formulations with the above provisos.

Example 1

Conditioner Shampoo with PQ-10

| | |
|---|---|
| 35.70 g | Sodium laureth sulfate |
| 6.50 g | Cocamidopropylbetaine |
| 0.20 g | Polymer according to example 1 |
| 0.40 g | Polyquaternium-10 |
| 0.10 g | Preservative |
| 0.10 g | Perfume oil/essential oil |
| ad 100 g | Aqua dem. |

Good conditioner shampoos are also obtained if, instead of the polymer according to example 1, the polymers of examples 2 or 3 are used.

Example 2

Conditioner Shampoo with GHTC

| | |
|---|---|
| 35.70 g | Sodium laureth sulfate |
| 6.50 g | Cocamidopropylbetaine |
| 0.50 g | Polymer according to example 1 |
| 0.20 g | Guar hydroxypropyltrimonium chloride |
| 0.10 g | Preservative |
| 0.10 g | Perfume oil/essential oil |
| ad 100 g | Aqua dem. |

Good conditioner shampoos are also obtained if, instead of the polymer according to example 1, the polymers of examples 2 or 3 are used.

Example 3

Conditioner Shampoo with Polyquaternium

| | |
|---|---|
| 35.70 g | Sodium laureth sulfate |
| 6.50 g | Cocamidopropylbetaine |
| 0.20 g | Polymer according to example 1 |
| 0.30 g | Polyquaternium-44 or PQ-67 |
| 0.10 g | Preservative |
| 0.10 g | Perfume oil/essential oil |
| ad 100 g | Aqua dem. |

Good conditioner shampoos are also obtained if, instead of the polymer according to example 1, the polymers of examples 2 or 3 are used.

Example 4

Shampoo

| | |
|---|---|
| Phase A | |
| 15.00 g | Cocamidopropylbetaine |
| 10.00 g | Disodium cocoamphodiacetate |
| 5.00 g | Polysorbate 20 |
| 5.00 g | Decyl glucoside |
| 0.20 g | Polymer according to example 1 |
| 0.10 g | Perfume oil/essential oil |
| q.s. | Preservative |
| 2.00 g | Laureth-3 |
| ad 100 | Aqua dem. |
| q.s. | Citric acid |
| Phase B | |
| 3.00 g | PEG-150 distearate |

Preparation

Weigh in components of phase A and dissolve; adjust pH to 6-7. Add phase B and heat to 50° C. Allow to cool to room temperature with stirring.

Good shampoos are also obtained if, instead of the polymer according to example 1, the polymers of examples 2 or 3 are used.

Example 5

Shampoo

| | |
|---|---|
| 30.00 g | Sodium laureth sulfate |
| 6.00 g | Sodium cocoamphoacetate |
| 0.50 g | Polymer according to example 1 |
| 3.00 g | Sodium laureth sulfate, glycol distearate, cocamide MEA, laureth-10 |
| 2.00 g | Dimethicone |
| q.s. | Perfume |
| q.s. | Preservative |
| q.s. | Citric acid |
| 1.00 g | Sodium chloride |
| ad 100 | Aqua dem. |

Good shampoos are also obtained if, instead of the polymer according to example 1, the polymers of examples 2 or 3 are used.

Example 6

Shower Gel

| | |
|---|---|
| 20.00 g | Ammonium laureth sulfate |
| 15.00 g | Ammonium lauryl sulfate |
| 0.50 g | Polymer according to example 1 |
| 0.50 g | Polyquaternium-7 |
| 2.50 g | Sodium laureth sulfate, glycol distearate, cocamide MEA, laureth-10 |

-continued

| | |
|---|---|
| 0.10 g | Perfume oil/essential oil |
| q.s. | Preservative |
| 0.50 g | Sodium chloride |
| ad 100 | Aqua dem. |

Good shower gels are also obtained if, instead of the polymer according to example 1, the polymers of examples 2 or 3 are used.

Example 7

Shower Gel

| | |
|---|---|
| 40.00 g | Sodium laureth sulfate |
| 5.00 g | Decyl glucoside |
| 5.00 g | Polymer according to example 1 |
| 1.00 g | Panthenol |
| 0.10 g | Perfume oil/essential oil |
| q.s. | Preservative |
| q.s. | Citric acid |
| 2.00 g | Sodium chloride |
| ad 100 | Aqua dem. |

Good shower gels are also obtained if, instead of the polymer according to example 1, the polymers of examples 2 or 3 are used.

Example 8

Shampoo

| | |
|---|---|
| 12.00 g | Sodium laureth sulfate |
| 1.50 g | Decyl glucoside |
| 0.50 g | Polymer according to example 1 |
| 5.00 g | Cocoglucoside glyceryl oleate |
| 2.00 g | Sodium laureth sulfate, glycol distearate, cocomide MEA, laureth-10 |
| q.s. | Preservative |
| q.s. | Sunset Yellow C.I. 15 985 |
| 0.10 g | Perfume oil/essential oil |
| 1.00 g | Sodium chloride |
| ad 100 | Aqua dem. |

Good shampoos are also obtained if, instead of the polymer according to example 1, the polymers of examples 2 or 3 are used.

The polymers suitable for the use according to the invention are also suitable for use in hairstyling preparations, in particular hair foams (aerosol foams with propellent gas and pump foams without propellent gas), hairsprays (pump sprays without propellent gas) and hair gels.

Propellants are the customarily used propellants. Preference is given to mixtures of propane/butane, pentane, dimethyl ether, 1,1-difluoroethane (HFC-152 a), carbon dioxide, nitrogen or compressed air.

Aerosol Hair Foam
a) 0.1 to 10% by weight of a cosmetic polymer
b) 55 to 99.8% by weight of water and/or alcohol
c) 5 to 20% by weight of a propellant
d) 0.1 to 5% by weight of a polymer suitable according to the invention
e) 0 to 10% by weight of further constituents Further constituents which may be used are, inter alia, all emulsifiers used customarily in hair foams. Suitable emulsifiers may be nonionic, cationic or anionic or amphoteric.

Examples of nonionic emulsifiers (INCI nomenclature) are laureths, e.g. laureth-4; ceteths, e.g. ceteth-1, polyethylene glycol cetyl ether; cetearaths, e.g. ceteareth-25, polyglycol fatty acid glycerides, hydroxylated lecithin, lactyl esters of fatty acids, alkyl polyglycosides.

Examples of cationic emulsifiers are cetyldimethyl-2-hydroxyethylammonium dihydrogenphosphate, cetyltrimonium chloride, cetyltrimonium bromide, cocotrimonium methyl sulfate, quaternium-1 to x (INCI).

Anionic emulsifiers can be selected, for example, from the group of alkyl sulfates, alkyl ether sulfates, alkylsulfonates, alkylarylsulfonates, alkyl succinates, alkyl sulfo-succinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule.

A preparation suitable according to the invention for styling gels can, for example, have the composition as follows:

Example 9

Aerosol Hair Foam

| | |
|---|---|
| 2.00 g | Cocotrimonium methosulfate |
| 0.10 g | Perfume oil/essential oil |
| 3.50 g | Setting polymer, e.g. Polyquaternium-46, PQ-44, VP/methacrylamide/vinyl-imidazole copolymer, etc. |
| 0.80 g | Polymer according to example 1 |
| q.s. | Preservative |
| 75.00 g | Water dem. |
| 10.00 g | Propane/butane (3.5 bar) |

Good aerosol hair foams are also obtained if, instead of the polymer according to example 1, the polymers of examples 2 or 3 are used.
Styling Gel
a) 0.1 to 10% by weight of a cosmetic polymer
b) 60 to 99.85% by weight of water and/or alcohol
c) 0.05 to 10% by weight of a gel former
d) 0.1 to 5% by weight of a polymer suitable according to the invention
e) 0 to 20% by weight of further constituents Gel formers which can be used are all gel formers customary in cosmetics. These include slightly crosslinked polyacrylic acid, for example carbomer (INCI), cellulose derivatives, e.g. hydroxypropylcellulose, hydroxyethylcellulose, cationically modified celluloses, polysaccharides, e.g. xanthan gum, caprylic/capric triglycerides, sodium acrylates copolymer, Polyquaternium-32 (and) paraffinum liquidum (INCI), sodium acrylates copolymer (and) paraffinum liquidum (and) PPG-1 trideceth-6, acrylamidopropyltrimonium chloride/acrylamide copolymer, steareth-10 allyl ether acrylates copolymer, Polyquaternium-37 (and) paraffinum liquidum (and) PPG-1 trideceth-6, Polyquaternium-37 (and) propylene glycol dicaprate dicaprylate (and) PPG-1 trideceth-6, Polyquaternium-7, Polyquaternium-44, Polyquaternium-67.

Good styling gels are also obtained if, instead of the polymer according to example 1, the polymers of examples 2 or 3 are used.

Example 10

Hairstyling Gel

| | Phase A |
|---|---|
| 0.50 g | Carbomer or acrylates/C10-30 alkyl acrylate crosspolymer |
| 86.40 g | Water dem. |
| | Phase B |
| 0.70 g | Triethanolamine |
| | Phase C |
| 6.00 g | Setting polymer, e.g. VP/methacrylamide/Vinylimidazole copolymer |
| 5.00 g | PVP |
| 0.20 g | PEG-25 PABA |
| 0.50 g | Polymer according to example 1 |
| 0.10 g | Perfume oil/essential oil |
| q.s. | PEG-14 dimethicone |
| q.s. | Preservative |
| 0.10 g | Tocopheryl acetate |

Good styling gels are also obtained if, instead of the polymer according to example 1, the polymers of examples 2 or 3 are used.

Example 11

Hairstyling Gel

| | Phase A |
|---|---|
| 0.50 g | Carbomer or acrylates/C10-30 alkyl acrylate crosspolymer |
| 91.20 g | Water dem. |
| | Phase B |
| 0.90 g | Tetrahydroxypropylethylenediamine |
| | Phase C |
| 7.00 g | VP/VA copolymer |
| 0.40 g | Polymer according to example 1 |
| 0.20 g | Perfume oil/essential oil |
| q.s. | Preservative |
| 0.10 g | Propylene glycol |

Good styling gels are also obtained if, instead of the polymer according to example 1, the polymers of examples 2 or 3 are used.

Example 12

Hair Wax Cream

| 6.00 g | Caprylic/capric triglycerides |
|---|---|
| 3.00 g | Glyceryl stearate |
| 2.00 g | Cetyl alcohol |
| 3.50 g | Polymer according to example 1 |
| 0.50 g | Cremophor A6 |
| 0.70 g | Cremophor A25 |

-continued

| 0.50 g | Dimethicone |
|---|---|
| 0.50 g | Vitamin E acetate |
| 2.00 g | Caprylic/capric triglycerides and sodium acrylates copolymer |
| 1.00 g | D-panthenol USP |
| 0.10 g | EDTA |
| 10.00 g | Setting polymer |
| q.s. | Preservative |
| ad 100 g | Water dem. |

Good hair wax creams are also obtained if, instead of the polymer according to example 1, the polymers of examples 2 or 3 are used.

Example 13

Hair Pudding

| 3.00 g | Kollicoat IR (BASF) |
|---|---|
| q.s. | Preservative |
| 2.00 g | Setting polymer |
| 4.00 g | Acrylates/beheneth-25 methacrylate copolymer |
| 0.70 g | Polymer according to example 1 |
| 0.50 g | Dimethicone copolyol |
| 0.10 g | EDTA |
| 0.20 g | Benzophenone-4 |
| ad 100 g | Water dem. |

Good hair puddings are also obtained if, instead of the polymer according to example 1, the polymers of examples 2 or 3 are used.

Example 14

Spray Gel

| | Phase A |
|---|---|
| 1.25 g | Setting polymer |
| 96.15 g | Aqua dem. |
| | Phase B |
| 0.70 g | Acrylates/steareth-20 itaconate copolymer |
| 0.10 g | Propylene glycol |
| 0.50 g | Polymer according to example 1 |
| 0.10 g | Glycerol |
| 0.10 g | Perfume oil/essential oil |
| q.s. | Preservative |
| | Phase C |
| 0.70 g | Triethanolamine |

Good spray gels are also obtained if, instead of the polymer according to example 1, the polymers of examples 2 or 3 are used.

A preparation suitable according to the invention for styling sprays can, for example, have the composition as follows:

Example 15

Pump Hair Spray

| | |
|---|---|
| 11.20 g | PEG/PPG-25/25 dimethicone/acrylates copolymer |
| 2.80 g | VP/VA copolymer |
| 1.34 g | Aminomethylpropanol |
| 0.30 g | Polymer according to example 1 |
| 0.10 g | Perfume oil/essential oil |
| 11.26 g | Aqua dem. |
| 73.00 g | Alcohol |

Good pump hair sprays are also obtained if, instead of the polymer according to example 1, the polymers of examples 2 or 3 are used.

Example 16

Pump Hair Spray VOC55

| | |
|---|---|
| 2.00 g | VP/methacrylamide/vinylimidazole copolymer |
| 1.90 g | Polyquaternium-46 |
| 2.00 g | Polymer according to example 1 |
| 0.10 g | Perfume oil/essential oil |
| 55.00 g | Alcohol |
| 39.00 g | Aqua dem. |

Good pump hair sprays VOC 55 are also obtained if, instead of the polymer according to example 1, the polymers of examples 2 or 3 are used.

Skin Cosmetic Compositions

Example 17

Liquid Makeup

| | |
|---|---|
| Phase A | |
| 1.70 g | Glyceryl stearate |
| 1.70 g | Cetyl alcohol |
| 1.70 g | Ceteareth-6 |
| 1.70 g | Ceteareth-25 |
| 5.20 g | Caprylic/capric triglycerides |
| 5.20 g | Mineral oil or Luvitol ® Lite |
| | (INCI Hydrogenated Polyisobutene) |
| Phase B | |
| q.s. | Preservative |
| 4.30 g | Propylene glycol |
| 2.50 g | Polymer according to example 1 |
| 59.50 g | Aqua dem. |
| Phase C | |
| 0.10 g | Perfume oil/essential oil |
| Phase D | |
| 2.00 g | Iron oxides |
| 12.00 g | Titanium dioxide |

Good liquid makeups are also obtained if, instead of the polymer according to example 1, the polymers of examples 2 or 3 are used.

Example 18

Eyeliner

| | |
|---|---|
| Phase A | |
| 40.60 g | dist. water |
| 0.20 g | Disodium EDTA |
| q.s. | Preservative |
| Phase B | |
| 0.60 g | Xanthan Gum |
| 0.40 g | Veegum |
| 3.00 g | Butylene glycol |
| 0.20 g | Polysorbate-20 |
| Phase C | |
| 15.00 g | Iron oxide/Al powder/silica |
| | (e.g. Sicopearl ® Fantastico Gold from BASF) |
| Phase D | |
| 10.00 g | Aqua dem. |
| 25.00 g | Setting polymer (e.g. polyurethane-1 or |
| | VP/methacrylamide/vinylimidazole copolymer, etc.) |
| 5.00 g | Polymer according to example 1 |

Good eyeliners are also obtained if, instead of the polymer according to example 1, the polymers of examples 2 or 3 are used.

Example 19

Sunscreen Gel

| | |
|---|---|
| Phase A | |
| 0.90 g | Polymer according to example 1 |
| 8.00 g | Octyl methoxycinnamate |
| 5.00 g | Octocrylene |
| 0.80 g | Octyltriazone |
| 2.00 g | Butylmethoxydibenzoylmethane |
| 2.00 g | Tocopheryl acetate |
| 0.10 g | Perfume oil/essential oil |
| Phase B | |
| 0.30 g | Acrylates/C10-30 alkyl acrylate crosspolymer |
| 0.20 g | Carbomer |
| 5.00 g | Glycerol |
| 0.20 g | Disodium EDTA |
| q.s. | Preservative |
| 75.30 g | Aqua dem. |
| Phase C | |
| 0.20 g | Sodium hydroxide |

Good sunscreen gels are also obtained if, instead of the polymer according to example 1, the polymers of examples 2 or 3 are used.

Example 20

Sunscreen Emulsion with $TiO_2$ and $ZnO_2$

| | Phase A |
|---|---|
| 1.00 g | PEG-7 hydrogenated castor oil |
| 5.00 g | Polymer according to example 1 |
| 2.00 g | PEG-45/dodecyl glycol copolymer |
| 3.00 g | Isopropyl myristate |
| 7.90 g | Jojoba (*Buxus Chinensis*) oil |
| 4.00 g | Octyl methoxycinnamate |
| 2.00 g | 4-Methylbenzylidenecamphor |
| 3.00 g | Titanium dioxide, dimethicone |
| 1.00 g | Dimethicone |
| 5.00 g | Zinc oxide, dimethicone |
| | Phase B |
| 0.20 g | Disodium EDTA |
| 5.00 g | Glycerol |
| q.s. | Preservative |
| 60.80 g | Aqua dem. |
| | Phase C |
| 0.10 g | Perfume oil/essential oil |

Good sunscreen emulsions are also obtained if, instead of the polymer according to example 1, the polymers of examples 2 or 3 are used.

Example 21

Face Tonics

| | Phase A |
|---|---|
| 3.00 g | Polymer according to example 1 |
| 0.10 g | Perfume oil/essential oil |
| 0.30 g | Bisabolol |
| | Phase B |
| 3.00 g | Glycerol |
| 1.00 g | Hydroxyethylcetyldimonium phosphate |
| 5.00 g | Witch Hazel (*Hamamelis Virginiana*) distillate |
| 0.50 g | Panthenol |
| q.s. | Preservative |
| 87.60 g | Aqua dem. |

Good face tonics are also obtained if, instead of the polymer according to example 1, the polymers of examples 2 or 3 are used.

Example 22

Face Washing Paste with Peeling Effect

| | Phase A |
|---|---|
| 73.00 g | Aqua dem. |
| 1.50 g | Carbomer |
| q.s. | Preservative |
| | Phase B |
| q.s. | Perfume oil |
| 7.00 g | Potassium cocoyl hydrolyzed protein |
| 4.00 g | Polymer according to example 1 |
| | Phase C |
| 1.50 g | Triethanolamine |
| | Phase D |
| 13.00 g | Polyethylene (Luwax A ™ from BASF) |

Good face washing pastes are also obtained if, instead of the polymer according to example 1, the polymers of examples 2 or 3 are used.

Example 23

Soap

| | Phase A |
|---|---|
| 25.00 g | Potassium cocoate |
| 20.00 g | Disodium cocoamphodiacetate |
| 2.00 g | Lauramide DEA |
| 1.0 g | Glycol stearate |
| 2.00 g | Polymer according to example 1 |
| 50.00 g | Aqua dem. |
| q.s. | Citric acid |
| | Phase B |
| q.s. | Preservative |
| 0.10 g | Perfume oil/essential oil |

Good soaps are also obtained if, instead of the polymer according to example 1, the polymers of examples 2 or 3 are used.

Example 24

Face Cleansing Milk O/W Type

| | Phase A |
|---|---|
| 1.50 g | Ceteareth-6 |
| 1.50 g | Ceteareth-25 |
| 2.00 g | Glyceryl stearate |
| 2.00 g | Cetyl alcohol |
| 10.00 g | Mineral oil |
| | Phase B |
| 5.00 g | Propylene glycol |
| q.s. | Preservative |
| 1.00 g | Polymer according to example 1 |
| 66.30 g | Aqua dem. |

-continued

| | Phase C |
|---|---|
| 0.20 g | Carbomer |
| 10.00 g | Cetearyl octanoate |
| | Phase D |
| 0.40 g | Tetrahydroxypropylethylenediamine |
| | Phase E |
| 0.10 g | Perfume oil/essential oil |
| 0.10 g | Bisabolol |

Good face cleansing milks are also obtained if, instead of the polymer according to example 1, the polymers of examples 2 or 3 are used.

Example 25

Transparent Soap

| 4.20 g | Sodium hydroxide |
|---|---|
| 3.60 g | dist. water |
| 10.00 g | Polymer according to example 1 |
| 22.60 g | Propylene glycol |
| 18.70 g | Glycerol |
| 5.20 g | Cocoamide DEA |
| 2.40 g | Cocamine oxide |
| 4.20 g | Sodium lauryl sulfate |
| 7.30 g | Myristic acid |
| 16.60 g | Stearic acid |
| 5.20 g | Tocopherol |

Good transparent soaps are also obtained if, instead of the polymer according to example 1, the polymers of examples 2 or 3 are used.

Example 26

Shaving Foam

| 6.00 g | Ceteareth-25 |
|---|---|
| 5.00 g | Poloxamer 407 |
| 52.00 g | Aqua dem. |
| 1.00 g | Triethanolamine |
| 5.00 g | Propylene glycol |
| 1.00 g | PEG-75 lanolin oil |
| 5.00 g | Polymer according to example 1 |
| q.s. | Preservative |
| 0.10 g | Perfume oil/essential oil |
| 25.00 g | Sodium laureth sulfate |

Bottling: 90 parts of active substance and 10 parts of a 25:75 propane/butane mixture.

Good shaving foams are also obtained if, instead of the polymer according to example 1, the polymers of examples 2 or 3 are used.

Example 27

Aftershave Balm

| | Phase A |
|---|---|
| 0.25 g | Acrylates/C10-30 alkyl acrylate crosspolymer |
| 1.50 g | Tocopheryl acetate |
| 0.20 g | Bisabolol |
| 10.00 g | Caprylic/capric triglycerides |
| q.s. | Perfume |
| 1.00 g | Polymer according to example 1 |
| | Phase B |
| 1.00 g | Panthenol |
| 15.00 g | Alcohol |
| 5.00 g | Glycerol |
| 0.05 g | Hydroxyethylcellulose |
| 1.90 g | Polymer according to example 1 |
| 64.02 g | dist. water |
| | Phase C |
| 0.08 g | Sodium hydroxide |

Good aftershave balms are also obtained if, instead of the polymer according to example 1, the polymers of examples 2 or 3 are used.

Example 28

Care Cream

| | Phase A |
|---|---|
| 2.00 g | Ceteareth-6 |
| 2.00 g | Ceteareth-25 |
| 2.00 g | Cetearyl alcohol |
| 3.00 g | Glyceryl stearate SE |
| 5.00 g | Mineral oil |
| 4.00 g | Jojoba (*Buxus Chinensis*) oil |
| 3.00 g | Cetearyl octanoate |
| 1.00 g | Dimethicone |
| 3.00 g | Mineral oil, lanolin alcohol |
| | Phase B |
| 5.00 g | Propylene glycol |
| 0.50 g | Veegum |
| 1.00 g | Panthenol |
| 1.70 g | Polymer according to example 1 |
| 6.00 g | Polyquaternium-44 |
| q.s. | Preservative |
| 60.80 g | Aqua dem. |
| | Phase C |
| q.s. | Perfume |

Good care creams are also obtained if, instead of the polymer according to example 1, the polymers of examples 2 or 3 are used.

Oral and Dental Care Preparations

Example 29

Toothpaste

| | Phase A |
|---|---|
| 34.79 g | Aqua dem. |
| 3.00 g | Polymer according to example 1 |
| 20.00 g | Glycerol |
| 0.76 g | Sodium monofluorophosphate |
| | Phase B |
| 1.20 g | Sodium carboxymethylcellulose |
| | Phase C |
| 0.80 g | Aroma oil |
| 0.06 g | Saccharin |
| q.s. | Preservative |
| 0.05 g | Bisabolol |
| 1.00 g | Panthenol |
| 0.50 g | Tocopheryl acetate |
| 2.80 g | Silica |
| 1.00 g | Sodium lauryl sulfate |
| 7.90 g | Dicalcium phosphate anhydrate |
| 25.29 g | Dicalcium phosphate dihydrate |
| 0.45 g | Titanium dioxide |

Good toothpastes are also obtained if, instead of the polymer according to example 1, the polymers of examples 2 or 3 are used.

Example 30

Mouthwash

| | Phase A |
|---|---|
| 2.00 g | Aroma oil |
| 4.50 g | Polymer according to example 1 |
| 1.00 g | Bisabolol |
| 30.00 g | Alcohol |
| | Phase B |
| 0.20 g | Saccharin |
| 5.00 g | Glycerol |
| q.s. | Preservative |
| 5.00 g | Poloxamer 407 |
| 52.30 g | Aqua dem. |

Good mouthwashes are also obtained if, instead of the polymer according to example 1, the polymers of examples 2 or 3 are used.

Example 37

Prosthesis Adhesive

| | Phase A |
|---|---|
| 0.20 g | Bisabolol |
| 1.00 g | Beta-carotene |
| q.s. | Aroma oil |
| 20.00 g | Cetearyl octanoate |
| 5.00 g | Silica |
| 33.80 g | Mineral oil |
| | Phase B |
| 5.00 g | Polymer according to example 1 |
| 35.00 g | PVP (20% strength solution in water) |

Good prosthesis adhesives are also obtained if, instead of the polymer according to example 1, the polymers of examples 2 or 3 are used.

Example 38

Liquid Soap

| 15.0 g | Coconut fatty acid, potassium salt |
|---|---|
| 3.0 g | Potassium oleate |
| 5.0 g | Luvitol ® Lite (BASF) |
| 2.0 g | Polymer of vinylpyrrolidone/stearyl methacrylate 70/30% by weight (K value 47; 1% in isopropanol) |
| 1.0 g | Glycerol stearate |
| 0.5 g | Polymer according to example 1 |
| 2.0 g | Ethylene glycol distearate |
| ad 100 | Specific additives, complexing agents, fragrances, water |

Good liquid soaps are also obtained if, instead of the polymer according to example 1, the polymers of examples 2 or 3 are used.

Examples 39-41

Conditioning Shampoo with Pearlescence

Data in % by Weight

| Additive | Ex. 39 | Ex. 40 | Ex. 41 |
|---|---|---|---|
| Polymer according to example 1 | 0.5 | 0.5 | 0.5 |
| Sodium laureth sulfate | 9.0 | 9.0 | 9.0 |
| Cocoamidopropylbetaine | 2.5 | 2.5 | 2.5 |
| Benzophenone-3 | 1.5 | 0.5 | 1.00 |
| Pearlizing agent | 2.0 | 2.0 | 2.0 |
| Luvitol Lite ®(BASF) | 0.1 | 0.15 | 0.05 |
| Disodium EDTA | 0.1 | 0.2 | 0.15 |
| Preservative, perfume, thickener, pH regulator and solubility promoter | q.s. | q.s. | q.s. |
| Water | ad 100.0 | ad 100.0 | ad 100.0 |

The pH is adjusted to 6.

Good conditioning shampoos with pearlescence are also obtained if, instead of the polymer according to example 1, the polymers of examples 2 or 3 are used.

Examples 42-46

Formulations for Showering, Washing, Bathing

Data in % by Weight

| Additive | Ex. 42 | Ex. 43 | Ex. 44 | Ex. 45 | Ex. 46 |
|---|---|---|---|---|---|
| Texapon N 70 | 13.00 | 15.00 | 10.50 | 12.50 | 10.00 |
| Dehyton PK 45 | 7.50 | 7.00 | 5.00 | 5.50 | 10.00 |

-continued

| Additive | Ex. 42 | Ex. 43 | Ex. 44 | Ex. 45 | Ex. 46 |
|---|---|---|---|---|---|
| Cetiol HE | 2.00 | 2.50 | 3.50 | 5.00 | 2.30 |
| Perfume | 0.10 | 0.10 | 0.10 | 0.10 | 0.10 |
| Luvitol ® Lite (BASF) | 1.00 | 4.50 | 7.00 | 1.40 | 3.00 |
| D-Panthenol USP | 1.00 | 1.50 | 1.80 | 1.70 | 1.40 |
| Preservative | 0.10 | 0.10 | 0.10 | 0.10 | 0.10 |
| Citric acid | 0.10 | 0.10 | 0.10 | 0.10 | 0.10 |
| Polymer according to example 1 | 0.50 | 1.00 | 0.50 | 0.20 | 0.10 |
| Sodium chloride | 1.50 | 1.40 | 1.40 | 1.30 | 1.50 |
| Water dem. | ad 100 | ad 100 | ad 100 | ad 100 | ad 100 |

Good formulations for showering, washing, bathing are also obtained if, instead of the polymer according to example 1, the polymers of examples 2 or 3 are used.

The invention claimed is:

1. A hair cosmetic preparation comprising a cationic polymer obtainable by free-radical copolymerization of:
    a) 60 to 99 mol % of at least one 1-vinylimidazole monomer of the general formula I which is quaternized to at least 60 mol %,

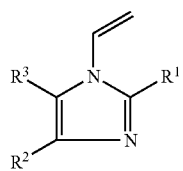

where $R^1$ to $R^3$, independently of one another, are hydrogen, $C_1$-$C_4$-alkyl or phenyl;
    b) 1 to 40 mol % of at least one free-radically polymerizable monomer selected from
    b1) optionally quaternized compounds selected from the group consisting of dimethylaminoethyl methacrylate and N-[3-(dimethylamino)propyl]methacrylamide, or a mixture thereof; and
    c) 0 to 30 mol % of a N-vinyllactam,
        where the total amount of the monomers a) to c) is 100 mol %.

2. The cationic polymer according to claim 1, where the cationic polymer is obtainable by free-radical polymerization of
    a) 65 to 90 mol % of monomer a)
    b) 5 to 35 mol % of monomer b)
    c) 0 to 20 mol % of monomer c),
        where the total amount of the monomers a) to c) is 100 mol %.

3. The cationic polymer according to claim 1, where the cationic polymer is obtainable by free-radical polymerization of
    a) 70 to 85 mol % of monomer a)
    b) 10 to 30 mol % of monomer b)
    c) 3 to 10 mol % of monomer c),
        where the total amount of the monomers a) to c) is 100 mol %.

4. The cationic polymer according to claim 1, where monomer a) is N-vinylimidazole.

5. The cationic polymer according to claim 1, where a) is quaternized to at least 70 mol %.

6. The hair cosmetic preparation according to claim 1, wherein the hair cosmetic preparation is a conditioner.

7. A method of cleansing hair or skin comprising applying the hair cosmetic preparation as defined in claim 1.

8. The method according to claim 7 wherein the hair cosmetic preparation is in the form of a haircare composition, shampoo or shower gel.

9. The cationic polymer according to claim 2, where the catonic polymer is obtainable by free-radical polymerization of
    a) 70 to 85 mol % of monomer a)
    b) 10 to 30 mol % of monomer b)
    c) 3 to 10 mol % of monomer c),
        where the total amount of the monomers a) to c) is 100 mol %.

10. The cationic polymer according to claim 2, where monomer a) is N-vinylimidazole.

11. The cationic polymer according to claim 3, where monomer a) is N-vinylimidazole.

12. The cationic polymer according to claim 2, where a) is quaternized to at least 70 mol %.

13. The cationic polymer according to claim 3, where a) is quaternized to at least 70 mol %.

14. The cationic polymer according to claim 4, where a) is quaternized to at least 70 mol %.

* * * * *